(12) United States Patent
Nakanishi et al.

(10) Patent No.: US 6,844,179 B1
(45) Date of Patent: Jan. 18, 2005

(54) PROTEIN AND DNA THEREOF

(75) Inventors: Atsushi Nakanishi, Tsukuba (JP); Shigeru Morita, Tsukuba (JP)

(73) Assignee: Takeda Chemical Industries, Ltd., Osaka (JP)

( * ) Notice: Subject to any disclaimer, the term of this patent is extended or adjusted under 35 U.S.C. 154(b) by 104 days.

(21) Appl. No.: 10/130,158

(22) PCT Filed: Nov. 14, 2000

(86) PCT No.: PCT/JP00/08015

§ 371 (c)(1),
(2), (4) Date: May 14, 2002

(87) PCT Pub. No.: WO01/36633

PCT Pub. Date: May 25, 2001

(30) Foreign Application Priority Data

Nov. 15, 1999 (JP) ............................................. 11/324467

(51) Int. Cl.[7] ............................. C12N 9/26; C12N 1/20; C12N 15/00; C12P 21/06; C07H 21/04
(52) U.S. Cl. ............................... 435/201; 435/4; 435/6; 435/69.1; 435/183; 435/200; 435/252.3; 435/320.1; 536/23.2; 536/23.5
(58) Field of Search ............................. 435/4, 6, 69.1, 435/183, 200–211, 252.3, 320.1; 536/23.2, 23.5, 23.4; 530/350; 424/94.1

(56) References Cited

PUBLICATIONS

Chang et al. (Genbank Accession No. S27879, Apr. 17, 1993).*
Saito et al (GenBank accession No. Q9ULY4, May 1, 2000.*
A Saito, et al. "Isolation and mapping of a human lung–specific gene, TSA 1902, encoding a novel chitinase family member" GENE 239: 325–31–No 2(1999).
M. Owhash. "Identification of a Novel Eosinophil Chemotactic Cytokine (ECF–L) as a Chitinase Family Protein" Journal of Biological Chemistry 275: 1279–86, No. 2 (2000).

* cited by examiner

Primary Examiner—Manjunath Rao
(74) Attorney, Agent, or Firm—Mark Chao; Elaine M. Ramesh

(57) ABSTRACT

The protein of the present invention and a DNA encoding the same can be used as therapeutic/prophylactic agents for diseases such as infectious diseases. The protein of the present invention is also useful as a reagent for screening a compound or its salt capable of promoting or inhibiting the activity of the protein of the present invention. Furthermore, a compound or its salt inhibiting the activity of the protein of the present invention and a neutralization antibody inhibiting the activity of the protein of the present invention can also be used as therapeutic/prophylactic agents for diseases such as bronchial asthma, chronic obstructive pulmonary disease, etc.

9 Claims, 11 Drawing Sheets

PROTEIN AND DNA THEREOF

This application is the National Phase filing of International Patent Application No. PCT/JP 00/08015, filed Nov. 14, 2000.

FIELD OF THE INVENTION

This invention relates to a novel protein and its DNA, which is useful as a diagnostic marker or a drug target for bronchial asthma, chronic obstructive pulmonary disease, etc., and also as a therapeutic agent, a prophylactic agent, or the like, for infectious diseases, immune deficiency, etc.

BACKGROUND ART

Bronchial asthma is a chronic inflammatory disease of airways showing respiratory stenosis, in which symptoms such as paroxysmal dyspnea, stridor, cough, etc. are observed. Many cells such as bronchial epithelial cells, mast cells, eosinophils, T lymphocytes, etc. are involved in its onset and development. One of the most important characteristics of bronchial asthma is that airways are hyperresponsive to irritants (airway hyperresponsiveness). This airway hyperresponsiveness is attributable to airway inflammation caused mainly due to exfoliation of bronchial epithelial cells by neurotransmitters secreted from the cells such as eosinophils, etc., infiltrated into airways, and it is also considered that genetic factors or environmental factors will affect the airway hyperresponsiveness complicatedly.

When the inflammatory reaction of airways is triggered by external irritants (allergens, exhausts) or viral infection, adhesion molecules including VCAM-1, ICAM-1 and the like are expressed on bronchial epithelial cells or on capillary endothelial cells around the bronchi [J. Allergy Clin. Immunol., 96, 941 (1995)] to produce cytokines or chemotactic substances. In patients with bronchial asthma, the function of Th2 type helper T cells is activated to increase the production of Th2 type cytokines such as IL-3, IL-4, IL-5, IL-13, GM-CSF, etc., or chemokines such as eotaxin, RANTES, etc. IL-4 or IL-13 has an activity of inducing IgE production, and IL-3 or IL-4 has an activity of inducing the growth of mast cells. Furthermore, eosinophils differentiate and proliferate in response to IL-5, GM-CSF, etc. and infiltrate into the airways in response to eotaxin or RANTES [Allergy Asthma Proc., 20, 141 (1999)].

Epithelial cells that cover the bronchial mucosa not only have the barrier function to prevent direct transmittance of external irritants to submucosal tissues and the function to excrete mucus secretions or foreign matters, but also regulate bronchoconstriction by secreted epithelium-derived smooth muscle relaxing factors, etc. Eosinophils infiltrated into the airways of patient with bronchial asthma release through degranulation of intracellular granule proteins such as activated MBP (major basic protein), ECP (eosinophil cationic protein), etc. [Compr. Ther., 20, 651 (1994)]. By the cytotoxic action of these granular proteins, the exfoliation and damages of epithelial cells occur. The exfoliation of epithelial cells leads to exposure of sensory nerve terminals, increase in epithelial permeability and loss of epithelium-derived smooth muscle relaxing factors. Also, leukotriene C4 (LTC4) or platelet activating factor (PAF) produced by eosinophils increase tension of bronchial smooth muscle. It is considered that when the foregoing changes are repeated to make it chronic, the bronchial walls would be thickened to cause airway hyperresponsiveness.

As stated above, it is known that genes of the cytokines or adhesion molecules described above are increasingly expressed, accompanied by inflammation of the airways, but there is no report to systematically analyze the change of genes, expression of which are localized in the lesion of lung/bronchi and which are associated with the onset of airway hyperresponsiveness.

On the other hand, chitinase activity was detected in blood plasma from patient with Gaucher's disease [J. Clin. Invest., 93, 1288 (1994)), the protein was purified as only one chitinase in mammal [J. Biol. Chem., 270, 2198 (1995)] and the gene was cloned [J. Biol. Chem., 270, 26252 (1995)]. This chitinase has been used as a disease marker but no relationship between bronchial asthma and chitinase has not been reported.

The present invention provides a novel protein, expression of which increases in the lung/bronchi having increased airway hyperresponsiveness, or salts thereof, its partial peptide or salts thereof, its signal peptide; a DNA encoding the protein, its partial peptide or signal peptide; recombinant vectors; transformants; methods of manufacturing the protein; pharmaceutical compositions comprising the protein or DNA; antibodies against the protein; methods for screening compounds that suppress or promote the expression of the protein; methods for screening compounds that suppress or promote the activity of the protein; compounds obtainable by the screening methods; etc.

DISCLOSURE OF THE INVENTION

The present inventors made extensive studies to solve the foregoing problems and as a result, discovered a gene, expression of which markedly increases in the lung/bronchi of mouse asthma model. Furthermore based on the base sequence of this gene, the inventors succeeded in cloning a cDNA having a novel base sequence from human gastric cDNA library, and found that a protein encoded by the cDNA belongs to the chitinase family.

Based on these findings, the inventors continued further investigations to accomplish the present invention.

That is, the present invention relates to the following features.

(1) A protein containing the same or substantially the same amino acid sequence as the amino acid sequence represented by SEQ ID NO:1, or a salt thereof.

(2) A partial peptide of the protein according to (1), or a salt thereof.

(3) A signal peptide having the same or substantially the same amino acid sequence as the amino acid sequence represented by SEQ ID NO:2, or a salt thereof.

(4) A DNA containing a DNA encoding the protein according to (1) or the partial peptide according to (2).

(5) The DNA according to (4) having a base sequence represented by SEQ ID NO:3.

(6) A DNA containing a DNA encoding the signal peptide according to (3).

(7) The DNA according to (6) having a base sequence represented by SEQ ID NO:4.

(8) A recombinant vector containing the DNA according to (4).

(9) A transformant transformed with the recombinant vector according to (8).

(10) A method of manufacturing the protein according to (1) or the partial peptide according to (2), or a salt thereof, which comprises culturing said transformant according to (9), producing/accumulating the protein according to (1) or the partial peptide according to (2), and collecting the same.

(11) A pharmaceutical comprising the protein according to (1) or the partial peptide according to (2) or a salt thereof.

(12) A pharmaceutical comprising the DNA according to (4).

(13) An antibody against the protein according to (1) or the partial peptide according to (2), or a salt thereof.

(14) A method of screening a compound or a salt thereof capable of promoting or inhibiting the activity of the protein according to (1) or the partial peptide according to (2), or a salt thereof, which comprises using the protein according to (1) or the partial peptide according to (2), or a salt thereof.

(15) A kit for screening a compound or a salt thereof capable of promoting or inhibiting the activity of the protein according to (1) or the partial peptide according to (2), or a salt thereof, comprising the protein according to (1) or the partial peptide according to (2), or a salt thereof.

(16) A compound or a salt thereof capable of promoting or inhibiting the activity of the protein according to (1) or the partial peptide according to (2), or a salt thereof, which is obtainable using the screening method according to (14) or the screening kit according to (15).

(17) A pharmaceutical comprising a compound or a salt thereof capable of promoting or inhibiting the activity of the protein according to (1) or the partial peptide according to (2), or a salt thereof, which is obtainable using the screening method according to (14) or the screening kit according to (15).

(18) A method of screening a compound or a salt thereof capable of inhibiting the activity of a protein containing the same or substantially the same amino acid sequence as the amino acid sequence represented by SEQ ID NO:18, its partial peptide, or a salt thereof, which comprises using the protein containing the same or substantially the same amino acid sequence as the amino acid sequence represented by SEQ ID NO:18, its partial peptide, or a salt thereof.

(19) A kit for screening a compound or a salt thereof capable of inhibiting the activity of a protein containing the same or substantially the same amino acid sequence as the amino acid sequence represented by SEQ ID NO:18, its partial peptide, or a salt thereof, comprising the protein containing the same or substantially the same amino acid sequence as the amino acid sequence represented by SEQ ID NO:18, its partial peptide, or a salt thereof.

(20) A compound or a salt thereof capable of inhibiting the activity of a protein containing the same or substantially the same amino acid sequence as the amino acid sequence represented by SEQ ID NO:18, its partial peptide, or a salt thereof, which is obtainable using the screening method according to (18) or the screening kit according to (19).

(21) A pharmaceutical comprising the compound or a salt thereof, according to (20).

BRIEF DESCRIPTION OF THE DRAWINGS

FIG. 7 shows comparison in base sequence between DNA (human ECF-L) encoding human-derived ECF-L like protein and mouse ECF-L gene (mouse ECF-L).

FIG. 8 shows comparison in amino acid sequence between human-derived ECF-L like protein (human ECF-L) and mouse ECF-L gene (mouse ECF-L).

FIG. 9 shows comparison in amino acid sequence between human-derived ECF-L like protein (human ECF-L) and other proteins (human chitotriosidase, human HC-gp39pit, human YKL-39) belonging to the chitinase family (continued to FIG. 10).

FIG. 10 shows comparison in amino acid sequence between human-derived ECF-L like protein (human ECF-L) and other proteins (human chitotriosidase, human HC-gp39prt, human YXL-39) belonging to the chitinase family (continued from FIG. 9).

BEST MODE FOR CARRYING OUT THE INVENTION

Figure 1:
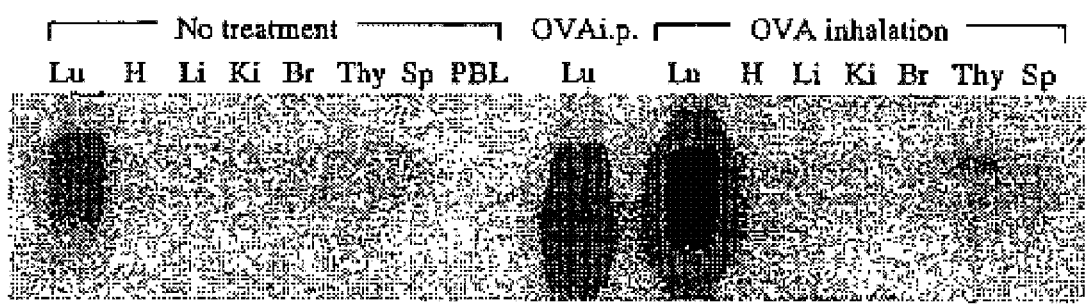
FIG. 1 shows tissue distribution of ECF-L gene (mRNA) in normal mouse and model mouse with increased airway hyperresponsiveness, in which Lu, H, Li, Ki, Br, Thy, Sp, SI, LI, St and PBL designate lung, heart, liver, kidney, brain, thymus, spleen, small intestine, large intestine, stomach and peripheral blood lymphocyte, respectively in EXAMPLE 2.
Figure 1:
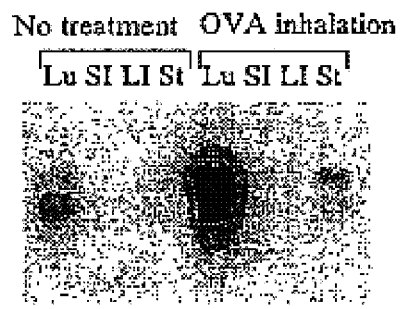

The protein of the present invention containing the same or substantially the same amino acid sequence as the amino acid sequence represented by SEQ ID NO:1 (hereinafter sometimes referred to as protein I of the invention) or the protein used in the present invention containing the same or substantially the same amino acid sequence as the amino acid sequence represented by SEQ ID NO:18 (hereinafter sometimes referred to as protein II) may be any protein derived from any cells of human and other warm-blooded animals (e.g., guineapig, rat, mouse, chicken, rabbit, swine, sheep, bovine, monkey, etc.) such as hepatocyte, splenocyte, nerve cells, glial cells, β cells of pancreas, bone marrow cells, mesangial cells, Langerhans' cells, epidermic cells, epithelial cells, goblet cells, endothelial cells, smooth musclecells, fibroblasts, fibrocytes, myocytes, fatcells, immune cells (e.g., macrophage, T cells, B cells, natural killer cells, mast cells, neutrophils, basophils, eosinophils, monocytes), megakaryocytes, synovial cells, chondrocytes, bone cells, osteoblasts, osteoclasts, mammary gland cells, hepatocyte or interstitial cells; or the corresponding precursor cells, stem cells, cancer cells, etc.; or any tissues where such cells are present, such as brain or any of brain regions (e.g., olfactory bulb, amygdaloid nucleus, basal ganglia, hippocampus, thalamus, hypothalamus, cerebral cortex, medulla oblongata, cerebellum), spinal cord, hypophysis, stomach, pancreas, kidney, liver, gonad, thyroid, gallbladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; the proteins may also be synthetic proteins.

As the amino acid sequence having substantially the same amino acid sequence as that shown by SEQ ID NO:1, there are amino acid sequences having at least about 80% homology, preferably at least about 90% homology and most preferably at least about 95% homology, to the amino acid sequence shown by SEQ ID NO:1.

Preferred examples of the protein containing substantially the same amino acid sequence as the amino acid sequence shown by SEQ ID NO:1 include proteins having substantially the same amino acid sequence as the amino acid sequence shown by SEQ ID NO:1 and having a property substantially equivalent to that of the protein having the amino acid sequence shown by SEQ ID NO:1, etc.

Examples of the properties substantially equivalent include an expression pattern, an expression timing, chitinase activity, and the like in the lung/bronchi. The substantially equivalent is used to mean that the nature of these properties is equivalent qualitatively. Preferably, the expression pattern, expression timing, chitinase activity, etc. in the lung/bronchi are equivalent, but differences in degree such as a level of these properties, quantitative factors such as a molecular weight of the protein may be present and allowable.

Examples of the protein I of the present invention include so-called muteins such as proteins containing 1) the amino acid sequence represented by SEQ ID NO:1, of which at least 1 or 2 (preferably about 1 to about 30, more preferably about 1 to about 10 and most preferably several (1 to 5)) amino acids are deleted; 2) the amino acid sequence represented by SEQ ID NO:1, to which at least 1 or 2 (preferably about 1 to about 30, more preferably about 1 to about 10 and most preferably several (1 to 5)) amino acids are added; 3) the amino acid sequence represented by SEQ ID NO:1, in which at least 1 or 2 (preferably about 1 to about 30, more preferably about 1 to about 10 and most preferably several (1 to 5)) aminoacids are inserted; 4) the amino acid sequence represented by SEQ ID NO:1, in which at least 1 or 2 (preferably about 1 to about 30, more preferably about 1 to about 10 and most preferably several (1 to 5)) amino acids are substituted by other amino acids; or 5) a combination of the above amino acid sequences.

As the amino acid sequence having substantially the same amino acid sequence as the amino acid sequence shown by SEQ ID NO:18, there are amino acid sequences having at least about 80% homology, preferably at least about 90% homology and most preferably at least about 95% homology, to the amino acid sequence shown by SEQ ID NO:18.

Preferred examples of the protein containing substantially the same amino acid sequence as the amino acid sequence shown by SEQ ID NO:18 include proteins having substantially the same amino acid sequence as the amino acid sequence shown by SEQ ID NO:18 and having a property substantially equivalent to that of the protein having the amino acid sequence shown by SEQ ID NO:18, etc.

Examples of the properties substantially equivalent include an expression pattern, an expression timing, and the like in the lung/bronchi. The substantially equivalent is used to mean that the nature of these properties is equivalent qualitatively. Preferably, the expression pattern, expression timing, etc. in the lung/bronchi are equivalent, but differences in degree such as a level of these properties, quantitative factors such as a molecular weight of the protein may be present and allowable.

Examples of the protein II of the present invention include so-called muteins such as proteins containing 1) the amino acid sequence represented by SEQ ID NO:18, of which at least 1 or 2 (preferably about 1 to about30, more preferably about 1 to about 10 and most preferably several (1 to 5)) amino acids are deleted; 2) the amino acid sequence represented by SEQ ID NO:18, to which at least 1 or 2 (preferably about 1 to about 30, more preferably about 1 to about 10 and most preferably several (1 to 5)) amino acids are added; 3) the amino acid sequence represented by SEQ ID NO:18, in which at least 1 or 2 (preferably about 1 to about 30, more preferably about 1 to about 10 and most preferably several (1 to 5)) amino acids are inserted; 4) the amino acid sequence represented by SEQ ID NO:18, in which at least 1 or 2 (preferably about 1 to about 3, more preferably about 1 to about 10 and most preferably several (1 to 5)) amino acids are substituted by other amino acids; or 5) a combination of the above amino acid sequences.

Throughout the specification, the proteins are represented in accordance with the conventional way of describing proteins, that is, the N-terminus (amino terminus) at the left hand and the C-terminus (carboxyl terminus) at the right hand. In the protein I or II of the present invention including the protein containing the amino acid sequence shown by SEQ ID NO:1 or SEQ ID NO:18, the C-terminus is usually in the form of a carboxyl group (—COOH) or a carboxylate (—COO$^-$) but may be in the form of an amide (—CONH$_2$) or an ester (—COOR).

Examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; pivaloyloxymethyl and the like.

Where the protein I or protein II of the present invention contains a carboxyl group (or a carboxylate) at a position other than the C-terminus, it may be amidated or esterified and such an amide or ester is also included within the protein I or II of the present invention. The ester group may be the same group as that described with respect to the above C-terminal.

Furthermore, examples of the protein I of the present invention include variants of the above proteins, wherein the amino group at the N-terminus (e.g., methionine residue) of the protein is protected with a protecting group (e.g., a $C_{1-6}$ acyl group such as a $C_{1-6}$ alkanoyl group, e.g., formyl group, acetyl group, etc.); those wherein the N-terminal region is cleaved in vivo and the glutamyl group thus formed is pyroglutaminated; those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains.

Specific examples of the protein I of the present invention include a human stomach-derived protein containing the amino acid sequence represented by SEQ ID NO:1, and the like.

Specific examples of the protein II of the present invention include a mouse-derived protein containing the amino acid sequence represented by SEQ ID NO:18, and the like.

The protein of the present invention containing the same or substantially the same amino acid sequence as the amino acid sequence represented by SEQ ID NO:1 further includes, for example, precursor proteins, in which at least one or two amino acids, preferably about 1 to about 200, more preferably about 1 to about 100, and most preferably about 1 to about 50, amino acids are conjugated at the N-terminus or (and) at the C-terminus of the protein I of the invention described above (hereinafter sometimes merely referred to as the precursor protein I of the invention).

The precursor protein I of the invention may be proteins derived from cells of, e.g., human and other warm-blooded animals (e.g., guineapig, rat, mouse, chicken, rabbit, swine, sheep, bovine, monkey, etc.) or any tissue in which these cells are present; or may also be synthetic proteins.

The precursor protein I of the invention may be any protein capable of producing the protein I of the invention described above. Thus, differences in quantitative factors such as a molecular weight of the protein may be present and allowable.

In the precursor protein I of the invention, the C-terminus is usually in the form of a carboxyl group (—COOH) or a carboxylate (—COO⁻) but may be in the form of an amide (—CONH$_2$) or an ester (—COOR) as in the protein I of the invention described above.

When the precursor protein I of the present invention contains carboxyl groups (or carboxylates) other than at the C-terminus, the precursor protein I further includes proteins wherein the carboxyl groups are amidated or esterified, those wherein the amino group of the N-terminal amino acid residue (e.g., methionine residue) is protected with a protecting group, those wherein the N-terminal region is cleaved in vivo and the glutamine thus formed is pyroglutaminated, those wherein a substituent on the side chain of an amino acid in the molecule is protected with a suitable protecting group, or conjugated proteins such as so-called glycoproteins to which sugar chains are bound, etc., as in the protein I of the present invention described above.

Specific examples of the precursor protein I of the present invention are a protein, in which the signal peptide of the present invention containing the amino acid sequence represented by SEQ ID NO:2 later described is bound at the N-terminus of the protein I of the present invention represented by SEQ ID NO:1 (i.e., a protein containing the amino acid sequence represented by SEQ ID NO:5), and the like.

For example, the precursor protein I of the present invention containing the signal peptide of the present invention later described is capable of efficiently secreting the protein I of the present invention extracellularly. The precursor protein I is also useful as an intermediate for manufacturing the protein I of the present invention.

The precursor protein I of the present invention can exhibit the activity similar to that of the protein I of the present invention, and can be used similarly to the protein I of the present invention.

The protein containing the same or substantially the same amino acid sequence as the amino acid sequence represented by SEQ ID NO:18 further includes, for example, precursor proteins, in which at least one or two amino acids, preferably about 1 to about 200, more preferably about 1 to about 100, and most preferably about 1 to about 50, amino acids are conjugated at the N-terminus or (and) at the C-terminus of the protein II described above (hereinafter sometimes merely referred to as the precursor protein II of the invention).

The precursor protein II can be proteins derived from cells of, e.g., human and other warm-blooded animals described above (e.g., guinea pig, rat, mouse, chicken, rabbit, swine, sheep, bovine, monkey, etc.) or any tissue in which these cells are present; or may also be synthetic proteins.

The precursor protein II may be any protein capable of producing the protein II described above. Thus, differences in quantitative factors such as a molecular weight of the protein may be present and allowable.

In the precursor protein II, the C-terminus is usually in the form of a carboxyl group (—COOH) or a carboxylate (—COO⁻) but may be in the form of an amide (—CONH$_2$) or an ester (—COOR) as in the protein II described above.

When the precursor protein II contains carboxyl groups (or carboxylates) other than at the C-terminus, the precursor protein II further includes proteins wherein the carboxyl groups are amidated or esterified, those wherein the amino group of the N-terminal amino acid residue (e.g., methionine residue) is protected with a protecting group, those wherein the N-terminal region is cleaved in vivo and the glutamine thus formed is pyroglutaminated, those wherein a substituent on the side chain of an amino acid in the molecule is protected with a suitable protecting group, or conjugated proteins such as so-called glycoproteins to which sugar chains are bound, etc., as in the protein II described above.

Specific examples of the precursor protein II are a protein, in which the signal peptide containing the amino acid sequence represented by SEQ ID NO:18 is bound at the N-terminus of the protein II represented by SEQ ID NO:1 (i.e., a protein containing the amino acid sequence represented by SEQ ID NO:17), and the like.

For example, the precursor protein II containing the signal peptide (1–21 amino acid residues in the amino acid sequence represented by SEQ ID NO:17) is capable of efficiently secreting the protein II extracellularly. The precursor protein II is also useful as an intermediate for manufacturing the protein II.

The precursor protein II can exhibit the activity similar to that of the protein II, and can be used similarly to the protein II.

The partial peptide (hereinafter sometimes merely referred to as the partial peptide I of the invention) of the protein I of the present invention may be any peptide as long as it is a partial peptide of the protein I of the present invention described above and preferably has the property equivalent to that of the protein I of the present invention described above. Examples of the partial peptide I include peptides containing at least 20, preferably at least 50, more preferably at least 70, much more preferably at least 100, and most preferably at least 200, amino acids in the constituent amino acid sequence of the protein I of the present invention, and the like.

The partial peptide I of the present invention may be peptides containing the amino acid sequence, of which at least 1 or 2 (preferably about 1 to about 10 and more preferably several (1 to 5)) amino acids are deleted; peptides, to which at least 1 or 2 (preferably about 1 to about 10 and more preferably several (1 to 5)) amino acids are added; peptides, in which at least 1 or 2 (preferably about 1 to about 10 and more preferably several (1 to 5)) amino acids are inserted; or peptides, in which at least 1 or 2 (preferably about 1 to about 10 and more preferably several (1 to 5)) amino acids are substituted by other amino acids.

In the partial peptide I of the invention, the C-terminus is usually in the form of a carboxyl group (—COOH) or a carboxylate (—COO⁻) but may be in the form of an amide (—CONH$_2$) or an ester (—COOR), as in the protein I of the present invention described above.

When the partial peptide I of the invention contains carboxyl groups (or carboxylates) other than at the C-terminus, the partial peptide I further includes proteins wherein the carboxyl groups are amidated or esterified, those wherein the amino group of the N-terminal amino acid residue (e.g., methionine residue) is protected with a protecting group, those wherein the N-terminal region is cleaved in vivo and the glutamine thus formed is pyroglutaminated, those wherein a substituent on the side chain of an amino acid in the molecule is protected with a suitable protecting group, or conjugated proteins such as so-called glycoproteins to which sugar chains are bound, etc., as in the protein I described above.

The partial peptide I of the invention may also be used as an antigen for producing antibodies.

The partial peptide (hereinafter sometimes merely referred to as the partial peptide II of the invention) of the protein II may be any peptide as long as it is a partial peptide of the protein II described above and preferably has the property equivalent to that of the protein II described above. Examples of the partial peptide II include peptides containing at least 20, preferably at least 50, more preferably at least 70, much more preferably at least 100, and most preferably at least 200, amino acids in the constituent amino acid sequence of the protein II, and the like.

The partial peptide II may be peptides containing the amino acid sequence, of which at least 1 or 2 (preferably about 1 to about 10 and more preferably several (1 to 5)) amino acids are deleted; peptides, to which at least 1 or 2 (preferably about 1 to about 10 and more preferably several (1 to 5)) amino acids are added; peptides, in which at least 1 or 2 (preferably about 1 to about 10 and more preferably several 11 to 5)) amino acids are inserted; or peptides, in which at least 1 or 2 (preferably about 1 to about 10 and more preferably several (1 to 5)) amino acids are substituted by other amino acids.

In the partial peptide II, the C-terminus is usually in the form of a carboxyl group (—COON) or a carboxylate (—COO$^-$) but may be in the form of an amide (—CONH$_2$) or an ester (—COOR) as in the protein II described above.

When the partial peptide II contains carboxyl groups (or carboxylates) other than at the C-terminus, the partial peptide II further includes proteins wherein the carboxyl groups are amidated or esterified, those wherein the amino group of the N-terminal amino acid residue (e.g., methionine residue) is protected with a protecting group, those wherein the N-terminal region is cleaved in vivo and the glutamine thus formed is pyroglutaminated, those wherein a substituent on the side chain of an amino acid in the molecule is protected with a suitable protecting group, or conjugated proteins such as so-called glycoproteins to which sugar chains are bound, etc., as in the protein II of the present invention described above.

The partial peptide II may also be used as an antigen for producing antibodies.

As the signal peptide of the present invention, there are employed those containing the same or substantially the same amino acid sequence as the amino acid sequence represented by, for example, SEQ ID NO:2, and the like (hereinafter sometimes merely referred to as the signal peptide I of the present invention).

The signal peptide I of the invention may be proteins derived from cells of, e.g., human and other warm-blooded animals described above (e.g., guinea pig, rat, mouse, chicken, rabbit, swine, sheep, bovine, monkey, etc.) or any tissue in which these cells are present; or may also be synthetic peptides.

As the amino acid sequence having substantially the same amino acid sequence as the amino acid sequence shown by SEQ ID NO:2, there are amino acid sequences having at least about 70% homology, preferably at least about 80% homology, more preferably at least about 90% and most preferably at least about 95% homology, to the amino acid sequence shown by SEQ ID NO:2. More specifically, the signal peptide may be any peptide having substantially the same amino acid sequence as the amino acid sequence shown by SEQ ID NO:2 and capable of exhibiting the function as a signal peptide. Thus, differences in quantitative factors such as a molecular weight of the protein may be present and allowable.

The signal peptide I of the present invention may be peptides containing the amino acid sequence, of which at least 1 or 2 (preferably about 1 to about 10 and more preferably several (1 to 5)) amino acids are deleted; peptides, to which at least 1 or 2 (preferably about 1 to about 10 and more preferably several (1 to 5)) amino acids are added; peptides, in which at least 1 or 2 (preferably about 1 to about 10 and more preferably several (1 to 5)) amino acids are inserted; or peptides, in which at least 1 or 2 (preferably about 1 to about 10 and more preferably several (1 to 5)) amino acids are substituted by other amino acids.

In the signal peptide I of the invention, the C-terminus is usually in the form of a carboxyl group (—COOH) or a carboxylate (—COO$^-$) but may be in the form of an amide (—CONH$_2$) or an ester (—COOR), as in the protein I of the present invention described above.

When the signal peptide I of the invention contains carboxyl groups (or carboxylates) other than at the C-terminus, the signal peptide I further includes proteins wherein the carboxyl groups are amidated or esterified, those wherein the amino group of the N-terminal amino acid residue (e.g., methionine residue) is protected with a protecting group, those wherein the N-terminal region is cleaved in vivo and the glutamine thus formed is pyroglutaminated, those wherein a substituent on the side chain of an amino acid in the molecule is protected with a suitable protecting group, or conjugated proteins such as so-called glycoproteins to which sugar chains are bound, etc., as in the protein I of the present invention described above.

Specific examples of the signal peptide I of the present invention are peptides containing the amino acid sequence represented by SEQ ID NO:2, in which the protein I of the present invention containing the amino acid sequence represented by SEQ ID NO:1 has been removed from the precursor protein I of the present invention containing the amino acid sequence represented by SEQ ID NO:5, and the like.

The signal peptide I of the present invention is capable of efficiently secreting a variety of extracellular secretory proteins including the protein I of the present invention extracellularly.

The protein I, precursor protein I, partial peptide I or signal peptide I, or protein II, precursor protein II, partial peptide II or signal peptide II, of the present invention may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The protein I, precursor protein I, partial peptide I or signal peptide I, or protein II, precursor protein II, partial peptide II or signal peptide II, of the present invention or salts thereof maybe manufactured by a publicly known method used to purify a protein from human or other warm-blooded animal cells or tissues described above. Alternatively, they may also be manufactured by culturing transformants containing DNAs encoding these proteins or peptides. Furthermore, they may also be manufactured by a modification of the methods for peptide synthesis, which will be described hereinafter.

Where these proteins or peptides are manufactured from human or mammalian tissues or cells, human or mammalian tissues or cells are homogenized, then extracted with an acid or the like, and the extract is isolated and purified by a combination of chromatography techniques such as reverse phase chromatography, ion exchange chromatography, and the like.

To synthesize the protein I, precursor protein I, partial peptide I or signal peptide I, or protein II, precursor protein II, partial peptide II or signal peptide II, of the present invention, or amides thereof, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl)phenoxy resin, etc. Using these resins, amino acids in which $\alpha$-amino groups and functional groups on the side chains are appropriately protected are condensed on the resin in the order of the sequence of the objective protein or peptide according to various condensation methods publicly known in the art. At the end of the reaction, the protein or peptide is excised from the resin and at the same time, the protecting groups are removed. Then, intramolecular disulfide bond-forming reaction is performed in a highly diluted solution to obtain the objective protein or peptide, or amides thereof.

For condensation of the protected amino acids described above, a variety of activation reagents for protein synthesis may be used, but carbodiimides are particularly preferably employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for protein condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitrites such as acetonitrile, propionitrile, etc.; esters such as methyl acetate, ethyl acetate, etc.; and appropriate mixtures of these solvents. The reaction temperature is appropriately chosen from the range known to be applicable to protein binding reactions and is usually selected in the range of approximately $-20°$ C. to $50°$ C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (in the form of linear, branched or cyclic alkyl esters of the alkyl moiety such as methyl, ethyl, propyl, butyl, t-butyl, cyclopentyl, cyclohexyl, cycloheptyl, cyclooctyl, 2-adamantyl, etc.), aralkyl esterification (e.g., esterification in the form of benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower $C_{1-6}$ alkanoyl group, such as acetyl group, an aroyl group such as benzoyl group, and a group derived from carbonic acid such as benzyloxycarbonyl group and ethoxycarbonyl group. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)). As the activated amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid or trifluoroacetic acid, or a mixture solution of these acids; a treatment with a base such as diisopropylethylamine, triethylamine, piperidine or piperazine; and reduction with sodium in liquid ammonia. The elimination of the protecting group by the acid treatment described above is carried out generally at a temperature of approximately $-20°$ C. to $40°$ C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol or 1,4-butanedithiol, as well as by a treatment with an alkali such as a dilute sodium hydroxide solution and dilute ammonia.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the amides of the desired protein or peptide, for example, the α-carboxyl group of the carboxy terminal amino acid is first protected by amidation; the peptide (protein) chain is then extended from the amino group side to a desired length. Thereafter, a protein or peptide, in which only the protecting group of the N-terminal α-amino group of the peptide chain has been eliminated, and a protein or peptide, in which only the protecting group of the C-terminal carboxyl group has been eliminated are manufactured. The two proteins or peptides are condensed in a mixture of the solvents described above. The details of the condensation reaction are the same as described above. After the protected protein or peptide obtained by the condensation is purified, all the protecting groups are eliminated by the method described above to give the desired crude protein or peptide. This crude protein or peptide is purified by various known purification means. Lyophilization of the major fraction gives the amide of the desired protein or peptide.

To prepare the esterified protein or peptide, for example, the α-carboxyl group of the carboxy terminal amino acid is condensed with a desired alcohol to prepare the amino acid ester, which is followed by procedure similar to the preparation of the amidated protein or peptide above to give the desired esterified protein or peptide.

The partial protein I, signal peptide I or partial peptide II, or salt thereof, of the present invention can be manufactured by publicly known methods for peptide synthesis, or by cleaving the protein I, precursor protein I, protein II or precursor protein II, of the present invention with an appropriate peptidase. For the methods for peptide synthesis, for example, either solid phase synthesis or liquid phase synthesis may be used. That is, the partial peptide or amino acids that can construct the partial peptide or signal peptide of the present invention are condensed with the remaining part. Where the product contains protecting groups, these protecting groups are removed to give the desired peptide. Publicly known methods for condensation and elimination of the protecting groups are described in 1) to 5) below.

1) M. Bodanszky & M. A. Ondetti: Peptide Synthesis, Interscience Publishers, New York (1966)

2) Schroeder & Luebke: The Peptide, Academic Press, New York (1965)

3) Nobuo Izumiya, et al.: *Peptide Gosel-no-Kiso to Jikken* (Basics and experiments of peptide synthesis), published by Maruzen Co. (1975)

4) Haruaki Yajima & Shunpei Sakakibara: *Seikagaku Jikken Koza* (Biochemical Experiment) 1, *Tanpakushitsu no Kagaku* (Chemistry of Proteins) IV, 205 (1977)

5) Haruaki Yajima ed.: Zoku zyakuhin no Kaihatsu (A sequel to Development of Pharmaceuticals), Vol. 14, Peptide Synthesis, published by Hirokawa Shoten After completion of the reaction, the product may be purified and isolated by a combination of conventional purification methods such as solvent extraction, distillation, column chromatography, liquid chromatography and recrystallization to give the protein or peptide of the present invention. When the protein or peptide obtained by the above methods is in a free form, the peptide can be converted into an appropriate salt by a publicly known method; when the protein is obtained in a salt form, it can be converted into a free form or other different salt form by a publicly known method.

The DNA encoding the protein I or protein II of the present invention may be any DNA so long as it contains the base sequence encoding the protein I or protein II of the present invention described above. The DNA may also be any one of genomic DNA, genomic DNA library, cDNA derived from the cells or tissues described above, cDNA library-derived from the cells or tissues described above and synthetic DNA.

The vector to be used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

Specifically, the DNA encoding the protein I of the present invention may be any one of, for example, a DNA having the base sequence represented by SEQ ID NO:3, or any DNA having a base sequence hybridizable to a DNA having the base sequence represented by SEQ ID NO:3 under high stringent conditions and encoding a protein which has the properties substantially equivalent to those of the protein I of the present invention. The DNA encoding the protein II of the present invention may be any one of, for example, a DNA containing the 72–1142 base sequence in the base sequence represented by SEQ ID NO:14, or any DNA having a base sequence hybridizable to a DNA containing the 72–1142 base sequence in the base sequence represented by SEQ ID NO:14 under high stringent conditions and encoding a protein which has the properties substantially equivalent to those of the protein II of the present invention.

Specific examples of the DNA that is hybridizable to DNA having the base sequence represented by SEQ ID NO:3 under high stringent conditions include DNAs having at least about 80% homology, preferably at least about 90% homology and most preferably at least about 95% homology, to the base sequence represented by SEQ ID NO:3.

Specific examples of the DNA that is hybridizable to DNA containing the 72–1142 base sequence in the base sequence represented by SEQ ID NO:14 under high stringent conditions include DNAs having at least about 80% homology, preferably at least about 90% homology and most preferably at least about 95% homology, to the 72–1142 base sequence in the base sequence represented by SEQ ID NO:14.

The hybridization can be carried out by publicly known methods or by a modification thereof, for example, according to the method described in Molecular Cloning, 2nd Ed., J. Sambrook et al., Cold Spring Harbor Lab. Press, (1989). A commercially available library may also be used according to the instructions of the attached manufacturer's protocol. The hybridization can be carried out preferably under high stringent conditions.

The high stringent conditions used herein are, for example, those in a sodium concentration at about 19 mM to about 40 mM, preferably about 19 mM to about 20 mM at a temperature of about 50° C. to about 70° C., preferably about 60° C. to about 6520 C. In particular, hybridization conditions in a sodium concentration at about 19 mM at a temperature of about 65° C. are most preferred.

More specifically, as the DNA encoding the protein having the amino acid sequence represented by SEQ ID NO:1, there may be employed a DNA containing a DNA having the base sequence represented by SEQ ID NO:3.

As the DNA encoding the protein having the amino acid sequence represented by SEQ ID NO:18, more specifically, a DNA containing a DNA having the 72–1142 base sequence in the base sequence represented by SEQ ID NO:14 maybe employed.

The DNA encoding the precursor protein I or precursor protein II of the present invention may be any DNA so long as it contains the base sequence encoding the precursor protein I or precursor protein II of the present invention described above. The DNA may also be any of genomic DNA, genomic DNA library, cDNA derived from the cells and tissues described above, cDNA library derived from the cells and tissues described above and synthetic DNA.

Specifically, the DNA encoding the precursor protein I of the present invention may be any one of, for example, a DNA having the base sequence represented by SEQ ID NO:16, or any DNA having a base sequence hybridizable to a DNA having the base sequence represented by SEQ ID NO:16 and encoding a protein capable of producing the protein I of the present invention described above.

The DNA encoding the precursor protein II may be, for example, a DNA containing the 9–1142 base sequence in the base sequence represented by SEQ ID NO:14, or a DNA having a base sequence hybridizable to the 9–1142 base sequence in the base sequence represented by SEQ ID NO:14 under high stringent conditions and encoding a protein capable of producing the protein II.

As the DNA hybridizable to the DNA having the base sequence represented by SEQ ID NO:16 under high stringent conditions, there are, for example, DNAs containing the base sequences having at least about 80% homology, preferably at least about 90% homology and most preferably at least about 95% homology, to the base sequence shown by SEQ ID NO:16.

As the DNA hybridizable to the DNA having the 9–1142 base sequence in the base sequence represented by SEQ ID NO:14under high stringent conditions, there are, for example, DNAs containing the base sequences having at least about 80% homology, preferably at least about 90% homology and most preferably at least about 95% homology, to the 9–1142 base sequence in the base sequence represented by SEQ ID NO:14.

Methods for the hybridization and the high stringent conditions that can be used are the same as those described above.

More specifically, DNAs containing a DNA having the base sequence represented by SEQ ID NO:16, and the like, are employed as the DNA encoding the precursor protein I of the present invention containing the amino acid sequence represented by SEQ ID NO:5.

As the DNA encoding the precursor protein II containing the amino acid sequence represented by SEQ ID NO:17, more specifically, DNAS containing DNAs having the 9–1142 base sequence in the base sequence represented by SEQ ID NO:14, and the like, are employed.

The DNA encoding the partial peptide I or partial peptide II of the present invention may be any peptide so long as it contains a base sequence encoding the partial peptide I or partial peptide II of the present invention described above.

The DNA may also be any one of genomic DNA, genomic DNA library, cDNA derived from the cells or tissues described above, cDNA library derived from the cells or tissues described above and synthetic DNA.

As the DNA encoding the partial peptide I of the present invention, there are employed, for example, a DNA having a part of the base sequence represented by SEQ ID NO:3, a DNA having a base sequence hybridizable to a DNA having the base sequence represented by SEQ ID NO:3 under high stringent conditions and containing a part of DNA encoding a protein having the properties substantially equivalent to those of the protein I of the present invention, and the like.

The DNA hybridizable to the DNA having the base sequence represented by SEQ ID NO:3 has the same significance as described above.

As the DNA encoding the partial peptide II, there are employed, for example, a DNA having a part of the 72–1142 base sequence in the base sequence represented by SEQ ID NO:14, a DNA having a base sequence hybridizable to a DNA having the 72–1142 base sequence in the base sequence represented by SEQ ID NO:14 under high stringent conditions and containing a part of DNA encoding a protein having the properties substantially equivalent to those of the protein II, and the like.

The DNA hybridizable to the DNA having the 72–1142 base sequence in the base sequence represented by SEQ ID NO:14 has the same significance as described above.

Methods for the hybridization and the high stringent conditions that can be used are the same as those described above.

The DNA encoding the signal peptide I of the present invention may be any peptide so long as it contains a base sequence encoding the signal peptide I of the present invention described above. The DNA may also be any one of genomic DNA, genomic DNA library, cDNA derived from the cells or tissues described above, cDNA library derived from the cells or tissues described above and synthetic DNA.

As the DNA encoding the signal peptide I of the present invention, there are employed, for example, a DNA having the base sequence represented by SEQ ID NO:4, a DNA having a base sequence hybridizable to a DNA having the base sequence represented by SEQ ID NO:4 under high stringent conditions and encoding a peptide capable of exhibiting the function as a signal peptide, and the like.

As the DNA hybridizable to the DNA having the base sequence represented by SEQ ID NO:4 under high stringent conditions, there are employed, for example, DNAs containing the base sequence having at least about 70% homology, preferably at least about 80% homology, more preferably at least about 90% homology and most preferably at least about 95% homology, to the base sequence represented by SEQ ID NO:4.

Methods for the hybridization and the high stringent conditions that can be used are the same as those described above.

More specifically, a DNA containing a DNA having the base sequence represented by SEQ ID NO:4, and the like, are employed as the DNA encoding the signal peptide I of the present invention containing the amino acid sequence represented by SEQ ID NO:2.

For cloning of DNAs that completely encode the protein I, precursor protein I, partial peptide I, signal peptide I, protein II, precursor protein II or partial peptide II, of the present invention (hereinafter sometimes merely referred to as the protein of the present invention), the DNA may be either amplified by publicly known PCR using synthetic DNA primers containing a part of the base sequence of the protein of the present invention, or the DNA inserted into an appropriate vector can be screened by hybridization with a labeled DNA fragment or synthetic DNA that encodes apart or entire region of the protein of the present invention. The hybridization can be carried out, for example, according to the method described in Molecular Cloning, 2nd (J. Sambrook et al., Cold Spring Harbor Lab. Press, 1989). Where the hybridization is carried out using commercially available library, the procedures may be conducted in accordance with the protocol described in the attached instructions.

Substitution of the base sequence of DNA can be effected by publicly known methods such as the ODA-LA PCR method, the Gapped duplex method or the Kunkel method or its modification by using a publicly known kit available as Mutant™-super Express Km or Mutan™-K (both manufactured by Takara Shuzo Co., Ltd., trademark), etc.

The cloned DNA encoding the protein of the present invention can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector of the protein of the present invention can be manufactured, for example, by (a) excising the desired DNA fragment from the DNA encoding the protein of the present invention, (b) and then ligating the DNA fragment with an appropriate expression vector downstream a promoter in the vector.

Examples of the vector include plasmids derived form $E.$ $coli$ (e.g., pBR322, pBR325, pUC12, pUC13), plasmids derived from $Bacillus\ subtilis$ (e.g., pUB110, pTP5, pC194), plasmids derived from yeast (e.g., pSH19, pSH15), bacteriophages such as $\lambda$ phage, etc., animal viruses such as retrovirus, vaccinia virus, baculovirus, etc. as well as as pA1-11, pXT1, pRc/CMV, pRc/RSV, pcDNAI/Neo, etc.

The promoter used in the present invention may be any promoter if it matches well with a host to be used for gene expression. In the case of using animal cells as the host, examples of the promoter include SR$\alpha$ promoter, SV40 promoter, LTR promoter, CMV promoter, HSV-TK promoter, etc.

Among them, CMV (cytomegalovirus) promoter or SR$\lambda$ promoter is preferably used. Where the host is bacteria of the genus Escherichia, preferred examples of the promoter include trp promoter, lac promoter, recA promoter, $\gamma$PL promoter, lpp promoter, T7 promoter, etc. In the case of using bacteria of the genus $Bacillus$ as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as AMp$^r$), neomycin resistant gene (hereinafter sometimes abbreviated as Neo, G418 resistance), etc. In particular, when dhfr gene is used as the selection marker using dhfr gene-deficient Chinese hamster cells, selection can also be made on a thymidine free medium.

If necessary, a signal sequence that matches with a host is added to the N-terminus of the protein of the present invention. Examples of the signal sequence that can be used are PhoA signal sequence, OmpA signal sequence, etc. in the case of using bacteria of the genus $Escherichia$ as the host; $\alpha$-amylase signal sequence, subtilisin signal sequence, etc. in the case of using bacteria of the genus $Bacillus$ as the host; MF$\alpha$ signal sequence, SUC2 signal sequence, etc. in the case of using yeast as the host; and insulin signal sequence, $\alpha$-interferon signal sequence, antibody molecule signal sequence, etc. in the case of using animal cells as the host, respectively.

Using the vector containing the DNA encoding the protein of the present invention thus constructed, transformants can be manufactured.

Examples of the host, which may be employed, are bacteria belonging to the genus $Escherichia$, bacteria belonging to the genus $Bacillus$, yeast, insect cells, insects and animal cells, etc.

Specific examples of the bacteria belonging to the genus $Escherichia$ include $Escherichia\ coli$ K12 DH1 [Proc. Natl. Acad. Sci. U.S.A., 60, 160 (1968)], JM103 (Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus $Bacillus$ include $Bacillus\ subtilis$ MI114 [Gene, 24, 255 (1983)], 207–21 [Journal of Biochemistry, 95, 87 (1984)], etc.

Examples of yeast include $Saccharomyces\ cereviseae$ AH22, AH22R$^-$, NA87-11A, DKD-5D, 20B-12, $Schizosaccharomyces\ pombe$ NCYC1913, NCYC2036, $Pichia\ pastoris$ KM71, etc.

Examples of insect cells include, for the virus AcNPV, $Spodoptera\ frugiperda$ cell (Sf cell), MG1 cell derived from mid-intestine of $Trichoplusia\ ni$, High Five™ cell derived from egg of $Trichoplusia\ ni$, cells derived from $Mamestra\ brassicae$, cells derived from $Estigmena\ acrea$, etc.; and for the virus BmNPV, $Bombyx\ mori$ N cell (BmN cell), etc. is used. Examples of the Sf cell which can be used are Sf9 cell (ATCC CRL1711), Sf21 cell (both cells are described in Vaughn, J. L. et al., In Vivo, 13, 213–217 (1977), etc.

As the insect, for example, a larva of Bombyx mori can be used [Maeda et al., Nature, 315, 592 (1985)].

Examples of animal cells include monkey cell COS-7, Vero, Chinese hamster cell CHO (hereinafter referred to as CHO cell), dhfr gene-deficient Chinese hamster cell CHO (hereinafter simply referred to as CHO (dhfr$^-$) cell), mouse L cell, mouse AtT-20, mouse myeloma cell, rat GH 3, human FL cell, etc.

Bacteria belonging to the genus $Escherichia$ can be transformed, for example, by the method described in Proc. Natl. Acad. Sci. U.S.A., 69,2110 (1972), Gene, 17,107 (1982), etc.

Bacteria belonging to the genus $Bacillus$ can be transformed, for example, by the method described in Molecular & General Genetics, 168, 111 (1979), etc.

Yeast can be transformed, for example, by the method described in Methods in Enzymology, 194, 182–187 (1991), Proc. Natl. Acad. Sci. U.S.A., 75, 1929 (1978), etc.

Insect cells or insects can be transformed, for example, according to the method described in Bio/Technology, 6, 47–55(1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263–267 (1995) (published by Shujunsha), or Virology, 52,456 (1973).

Thus, the transformants transformed with the expression vectors containing the DNAs encoding the protein of the present invention can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, etc. Examples of the carbon sources include glucose, dextrin, soluble starch, sucrose, etc.; examples of the nitrogen sources include inorganic or organic materials such as ammonium salts, nitrate salts, corn steep liquor, peptone, casein, meat extract, soybean cake, potato extract, etc.; and, examples of the inorganic materials are calcium chloride, sodium dihydrogenphosphate, magnesium chloride, etc. In addition, yeast, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431–433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15° C. to about 43° C. for about 3 hours to about 24 hours. If necessary, the culture maybe aerated or agitated.

Where the bacteria belonging to the genus *Bacillus* are used as the host, the transformant is cultured generally at about 30° C. to about 40° C. for about 6 hours to about 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to about 8. In general, the transformant is cultivated at about 20° C. to about 35° C. for about 24 hours to about 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultured in, for example, MEM medium containing about 5% to about 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 hours to about 60 hours and, if necessary, the culture can be aerated or agitated.

As described above, the protein of the present invention can be produced in the cell membrane of the transformant.

The protein of the present invention can be separated and purified from the culture described above by the following procedures.

When the protein of the present invention is extracted from the culture or cells, the transformant or cell is collected after culturing by a publicly known method and suspended in a appropriate buffer. The transformant or cell is then disrupted by publicly known methods such as ultrasonication, a treatment with lysozyme and/or freeze-thaw cycling, followed by centrifugation, filtration, etc. Thus, the crude extract of the protein can be obtained. The buffer used for the procedures may contain a protein modifier such as urea or guanidine hydrochloride, or a surfactant such as Triton X-100™, etc. When the protein of the present invention is secreted in the culture broth, the supernatant can be separated, after completion of the cultivation, from the transformant or cell to collect the supernatant by a publicly known method.

The supernatant or the protein of the present invention contained in the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the protein of the present invention thus obtained is in a free form, the protein can be converted into the salt by publicly known methods or modifications thereof. On the other hand, when the protein is obtained in the form of a salt, it can be converted into the free form or in the form of a different salt by publicly known methods or modifications thereof.

The protein of the present invention produced by the recombinant can be treated, prior to or after the purification, with an appropriate protein-modifying enzyme so that the protein can be appropriately modified to partially remove the polypeptide. Examples of the protein-modifying enzyme include trypsin, chymotrypsin, arginyl endopeptidase, protein kinase, glycosidase and the like.

The presence of the thus produced protein of the present invention can be determined by a binding test to a labeled ligand and by an enzyme immunoassay using a specific antibody.

The antibodies to the protein I, precursor protein I, partial peptide I, protein II, precursor protein II, partial peptide II, or its salts, of the present invention may be any of polyclonal and monoclonal antibodies, as long as they are capable of recognizing the protein I, precursor protein I, partial peptide I, protein II, precursor protein II, partial peptide II, or its salts, of the present invention.

The antibodies to the protein I, precursor protein I, partial peptide I, protein II, precursor protein II, partial peptide II, or its salts, of the present invention (hereinafter these are sometimes referred to collectively as the protein of the invention) may be produced by a publicly known method of producing an antibody or antiserum, using the protein of the invention as an antigen.

[Preparation of Monoclonal Antibody]

(a) Preparation of Monoclonal Antibody-producing Cells

The protein of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every two to six weeks and two to ten times in total. Examples of the applicable warm-blooded animals are monkeys, rabbits, dogs, guinea pigs, mice, rats, sheep, goats and chickens, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after two to five days from the final immunization and antibody-producing cells contained therein-are fused with myeloma cells from homozoic or heterozoic animal to give monoclonal antibody-producing hybridomas. Measurement of the antibody titer in antisera may be carried out, for example, by reacting a labeled protein, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion accelerator are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at 20 to 40° C., preferably at 30 to 37° C. for 1 to 10 minutes, an efficient cell fusion can be carried out.

Various methods can be used for screening of monoclonal antibody-producing hybridomas. Examples of such methods include a method which comprises adding the supernatant of a hybridoma to a solid phase (e.g., a microplate) adsorbed with the protein as an antigen directly or together with a carrier, adding an anti-immunoglobulin antibody (where mouse cells are used for the cell fusion, anti-mouse immunoglobulin antibody is used) labeled with a radioactive substance or an enzyme or Protein A and detecting the monoclonal antibody bound to the solid phase, and a method which comprises adding the supernatant of hybridoma to a solid phase adsorbed with an anti-immunoglobulin antibody or Protein A, adding the protein labeled with a radioactive substance or an enzyme and detecting the monoclonal antibody bound to the solid phase, or the like.

The monoclonal antibody can be screened according to publicly known methods or their modifications. In general, the screening can be effected in a medium for animal cells supplemented with HAT (hypoxanthine, aminopterin and thymidine). Any screening and growth medium can be employed as far as the hybridoma can grow there. For example, RPMI 1640 medium containing 1% to 20%, preferably 10% to 20% fetal bovine serum, GIT medium (Wako Pure Chemical Industries, Ltd.) containing 1 to 10% fetal bovine serum, a serum free medium for cultivation of a hybridoma (SFM-101, Nissui seiyaku Co., Ltd.) and the like, can be used for the screening and growth medium. The culture is carried out generally at 20° C. to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody.]

[Preparation of Polyclonal Antibody]

The polyclonal antibody of the present invention can be manufactured by publicly known methods or modifications thereof. For example, a warm-blooded animal is immunized with an immunogen (protein antigen) per se, or a complex of immunogen and a carrier protein is formed and a warm-blooded animal is immunized with the complex in a manner similar to the method described above for the manufacture of monoclonal antibodies. The product containing the antibody to the protein of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to about 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every 2 to 6 weeks and 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The antisense DNA having a complementary or substantial complementary base sequence to the DNA encoding the protein I, precursor protein I, partial peptide I, signal peptide I, protein II, precursor protein II or partial peptide II, of the present invention (hereinafter these DNAs are sometimes collectively referred to as the DNA of the present invention in the following description of antisense DNA) can be any antisense DNA, so long as it possesses a base sequence complementary or substantially complementary to that of the DNA of the present invention and capable of suppressing expression of the DNA.

The base sequence substantially complementary to the DNA of the present invention may, for example, be a base sequence having at least about 70% homology, preferably at least about 80% homology, more preferably at least about 90% homology and most preferably at least about95% homology, to the full-length base sequence or partial base sequence of the base sequence complementary to the DNA of the present invention (i.e., complementary strand to the DNA of the present invention), and the like. In the entire base sequence of the complementary strand to the DNA of the present invention, an antisense DNA having at least about 70% homology, preferably at least about 80% homology, more preferably at least about 90% homology and most preferably at least about 95% homology, to the complementary strand of the base sequence which encodes the N-terminal region of the protein of the present invention (e.g., the base sequence around the initiation codon). These antisense DNAs can be synthesized using a publicly known DNA synthesizer, etc.

Hereinafter, the protein I, precursor protein I or partial peptide I, or its salts, of the present invention (hereinafter sometimes merely referred to as the protein a of the present invention), the protein II, precursor protein II or partial peptide II, or salts thereof (hereinafter sometimes merely referred to as the protein b of the present invention), the DNA encoding the protein a (hereinafter sometimes merely referred to as the DNAa of the present invention), the DNA encoding the protein b (hereinafter sometimes merely referred to as the DNAb of the present invention), the antibody to the protein I, precursor protein I, partial peptide I, protein II, precursor protein II, partial peptide II or signal peptide I, or salts thereof (hereinafter sometimes merely referred to as the antibody of the present invention) and the antisense DNA are explained with respect to the utilities. The protein a and protein b of the present invention are sometimes collectively referred to as the protein of the present invention, and the DNAa and DNAb of the present invention are sometimes collectively referred to the DNA of the present invention.

The protein a and protein b of the present invention can be utilized as disease markers, since expression of these proteins increases tissue-specifically in the lung/bronchi in asthma model animals. That is, these proteins are useful as markers for early diagnosis in lung/chest diseases accompanied by inflammation of the lung/airways, judgment of severity in conditions, or predicted development of diseases.

(1) Therapeutic and Prophylactic Agent for the Diseases with which the Protein a of the Present Invention Is Associated The protein a of the present invention is a member of the chitinase family. A chitinase is important for the biological protection mechanism against outward pathogens such as bacteria, virus, etc. Thus, the protein a of the present invention or the DNAa of the present invention may be used as a therapeutic/prophylactic agent for various diseases including immune diseases (e.g., autoimmune disease, immunodeficiency, allergic disease, etc.), infectious diseases (e.g., HIV (human immunodeficiency virus) infection, HBV (hepatitis B virus) infection, HCV (hepatitis C virus) infection, tuberculosis infection, opportunistic infection, etc.), and the like.

When a patient has a reduced level of, or deficient in the protein a, etc. of the present invention in his or her body where the biological protection mechanism is not exhibit sufficiently or normally, the protein a of the present invention can provide its role sufficiently or properly for the patient; (a) by administering the DNAa of the present invention to the patient to express the protein of the present invention in the body, (b) by inserting the DNAa of the present invention into a cell, expressing the protein of the present invention and then transplanting the cell to the patient, (c) by administering the protein a of the present invention to the patient, or the like.

Where the DNAa of the present invention is used as the therapeutic/prophylactic agents described above, the DNA alone is administered directly to human or other warm-blooded animal; alternatively, the DNA is inserted into an appropriate vector such as retrovirus vector, adenovirus vector, adenovirus-associated virus vector, etc. and then administered to human or other warm-blooded animal in a conventional manner. The DNAa of the present invention may also be administered as it is, or with adjuvants to assist its uptake by gene gun or through a catheter such as a catheter with a hydrogel.

Where the protein a of the present invention is used as the aforesaid therapeutic/prophylactic agents, it is preferred to use the same on a purified level of at least 90%, preferably at least 95%, more preferably at least 98% and most preferably at least 99%.

The protein a of the present invention can be used orally, for example, in the form of tablets which maybe sugar coated if necessary, capsules, elixirs, microcapsules, etc., or parenterally in the form of injectable preparations such as a sterile solution and a suspension in water or with other pharmaceutically acceptable liquid. These preparations can be prepared by mixing the protein a of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin and alginic acid, a lubricant such as magnesium stearate, a sweetening agent such as sucrose, lactose and saccharin, and a flavoring agent such as peppermint, akamono oil or cherry. When the unit dosage is in the form of capsules, liquid carriers such as oils and fats may further be used together with the additives described above. A sterile composition for injection may be formulated according to a conventional manner used to make a pharmaceutical, e.g., by dissolving or suspending the active ingredients in a vehicle such as water for injection with a naturally occurring vegetable oil such as sesame oil and coconut oil, etc. to prepare the pharmaceutical.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™, HCO-50, etc.), and the like. Examples of the oily medium include sesame oil, soybean oil, etc., which may also be used in combination with a dissolution aid such as benzyl benzoate, benzyl alcohol, etc. The agent may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector in which the DNAa of the present invention is inserted may also be prepared into pharmaceutical preparations in a manner similar to the procedures above. Such preparations are generally used parenterally.

Since the thus obtained pharmaceutical preparation is safe and low toxic, the preparation can be administered to human or other warm-blooded animal (e.g., rat, mouse, guinea pig, rabbit, chicken, sheep, swine, bovine, horse, cat, dog, monkey, chimpanzee, etc.).

The dose of the protein a of the present invention varies depending on target disease, subject to be administered, route for administration, etc.; for example, in oral administration for the treatment of infectious diseases, the dose is normally about 0.1 mg to about 100 mg, preferably about 1.0 to about 50 mg, and more preferably about 1.0 to about 20 mg per day for adult (as 60 kg body weight). In parenteral administration, the single dose varies depending on subject to be administered, target disease, etc. but it is advantageous for the treatment of infectious diseases to administer the protein intravenously at a daily dose of about 0.01 to about 30 mg, preferably about 0.1 to about 20 mg, and more preferably about 0.1 to about 10 mg for adult (as 60 kg body weight). For other animal species, the corresponding dose as converted per 60 kg body weight can be administered.

(2) Screening of Drug Candidate Compounds for Disease

Because the protein a of the present invention belongs to the chitinase family, a compound or its salt capable of promoting the activities (e.g., a chitinase activity, etc.) of the protein a of the present invention can be used as medicaments for the treatment/prevention of various diseases including immune diseases (e.g., autoimmune disease, immunodeficiency, allergic disease, etc.), infectious diseases (e.g., HIV infection, HBV infection, HCV infection, tuberculosis infection, opportunistic infection, etc.), and the like.

On the other hand, the protein a of the present invention is increasingly expressed prior to inflammation of the lung/bronchi, and can thus be used as medicaments for the treatment/prevention of lung/chest diseases accompanied by inflammation of the lung/airways, including bronchial asthma, chronic obstructive pulmonary disease, etc.

Therefore, the protein a of the present invention is useful as a reagent for screening the compound or its salts capable of promoting or inhibiting the activities of the protein a of the present invention.

That is, the present invention provides:

(1) a method for screening the compound or its salts capable of promoting the activities (e.g., a chitinase activity, etc.) of the protein I, precursor protein I or partial peptide I, or its salts, of the present invention (hereinafter sometimes merely referred to as the promoter), or the compound or its salts capable of inhibiting the activities of the protein I, precursor protein I or partial peptide I, or its salts, of the present invention (hereinafter sometimes merely referred to as the inhibitor), which comprises using the protein I, precursor protein I or partial peptide I, or its salts, of the present invention. More specifically, the present invention provides, e.g.,:

(2) a method for screening the promoter or the inhibitor, which comprises comparing (i) the case where a chitinase substrate is brought into contact with the protein I, precursor protein I or partial peptide I, or its salts, of the present invention and (ii) the case where a chitinase substrate and a test compound are brought into contact with the protein I, precursor protein I or partial peptide I, or its salts, of the present invention.

Specifically, in the screening method described above, the method is characterized by measuring, e.g., the chitinase activity of the protein a of the present invention in the cases (i) and (ii), and comparing the cases.

Examples of the substrate used are 4-methylumbelliferyl β-D-N,N'-diacetylchitobiose, 4-methylumbelliferyl β-D-N,N',N"-triacetylchitobiose, p-nitrophenyl β-D-N,N',N"-triacetylchitobiose, chitin azure, etc.

Examples of the test compound are a peptide, a protein, anon-peptide compound, a synthetic compound, a fermentation product, a cell extract, a plant extract, an animal tissue extract and the like. These compounds may be novel compounds or publicly known compounds.

To perform the screening method described above, the protein a of the present invention is suspended in a buffer suitable for screening to prepare a specimen for the protein a of the present invention. Any buffer having pH of approximately 4 to 10 (desirably a pH of approximately 6 to 8) such as a phosphate buffer, Tris-hydrochloride buffer, etc. may be used, so long as it does not interfere the reaction between the protein a of the present invention and the substrate.

The chitinase activity of the protein a of the present invention can be determined by a publicly known method described in, e.g., J. Biol. Chem., 270, 2198 (1995), or its modification.

For example, when a test compound increases the chitinase activity in (ii) described above by at least about 20%, preferably at least 30%, more preferably at least about 50%, as compared to the case of (i) above, the test compound can be screened to be a compound capable of promoting the chitinase activity of the protein a of the present invention. On the other hand, a test compound can be screened to be a compound capable of inhibiting the chitinase activity of the protein a of the present invention, when the test compound inhibits the chitinase activity in (ii) described above by at least about 20%, preferably at least 30%, more preferably at least about 50%, as compared to the case of (i) above.

The kit for screening according to the present invention comprises the protein I, precursor protein I or partial peptide I, or its salts, of the present invention.

The compounds or salts thereof obtained using the screening methods or screening kits of the present invention are compounds screened: from the test compounds described above, for example, peptides, proteins, non-peptide compounds, synthetic compounds, fermentation products, cell extracts, plant extracts, animal tissue extracts, blood plasma, etc., and are the compounds capable of promoting or inhibiting the activities (e.g., a chitinase activity, etc.) of the protein a of the present invention.

As salts of these compounds, there may be employed the same salts as those of the protein I of the present invention described above.

The compounds capable of promoting the activities (e.g., a chitinase activity, etc.) of the protein a of the present invention can be used as medicaments for the treatment/prevention of various diseases including immune diseases (e.g., autoimmune disease, immunodeficiency, allergic disease, etc.), infectious diseases (e.g., HIV infection, HBV infection, HCV infection, tuberculosis infection, opportunistic infection, etc.), and the like.

On the other hand, the compounds capable of inhibiting the activities of the protein a of the present invention can be used as medicaments for the treatment/prevention of lung/chest diseases accompanied by inflammation of the lung/airways, including bronchial asthma, chronic obstructive pulmonary disease, etc.

When the compounds obtained using the screening methods or screening kits of the present invention are used as the therapeutic/prophylactic agents described above, they can be used in a conventional manner. The compounds maybe used, for example, in the form of tablets, capsules, elixirs, microcapsules, a sterile solution, a suspension, etc., as in the pharmaceuticals containing the protein a of the present invention described above.

Since the thus obtained pharmaceutical preparation is safe and low toxic, the preparation can be administered to human or other warm-blooded animal (e.g., mouse, rat, rabbit, sheep, swine, bovine, horse, chicken, cat, dog, monkey, chimpanzee, etc.).

The dose of the compound or salts thereof varies depending on its action, target disease, subject to be administered, route for administration, etc.; when the compound capable of inhibiting the activity of the protein a of the present invention is orally administered for the treatment of, e.g., bronchial asthma, the compound is normally administered in a dose of about 0.1 to about 100 mg, preferably about 1.0 to about 50 mg, and more preferably about 1.0 to about 20 mg per day for adult (as 60 kg body weight). In parenteral administration, a single dose of the compound varies depending on subject to be administered, target disease, etc. but it is advantageous for the treatment of bronchial asthma to administer the compound capable of inhibiting the activity of the protein a of the present invention intravenously in the form of injection in a daily dose of about 0.01 to about 30 mg, preferably about 0.1 to about 20 mg, and more preferably about 0.1 to about 10 mg for adult (as 60 kg body weight). For other animal species, the corresponding dose as converted per 60 kg body weight can be administered.

On the other hand, when the compound capable of promoting the activity of the protein a of the present invention is orally administered for the treatment of infectious diseases, the compound is normally administered in a dose of about 0.1 to about 100 mg, preferably about 1.0 to about 50 mg, and more preferably about 1.0 to about 20 mg per day for adult (as 60 kg body weight). In parenteral administration, a single dose of the compound varies depending on subject to be administered, target disease, etc. but it is advantageous for the treatment of infectious diseases to administer the compound capable of promoting the activity of the protein a of the present invention intravenously in the form of injection in a daily dose of about 0.01 to about 30mg, preferably about 0.1 to about 20 mg, and more preferably about 0.1 to about 10 mg for adult (as 60 kg body weight) For other animal species, the corresponding dose as converted per 60 kg body weight can be administered.

(3) Screening of Drug Candidate Compounds for the Diseases with which the Protein a or Protein b of the Present Invention Is Associated The protein of the present invention is a secretory protein; for example, the protein II is produced in the lung/airways of mouse asthma model prior to inflammation, and thus considered to be associated with infiltration or activation of eoginophil, macrophage, etc. Therefore, the compound or its salt capable of inhibiting the activities of the protein a or protein b of the present invention can be employed as medicaments for the treatment/prevention of lung/chest diseases accompanied by inflammation of the lung/airways, including bronchial asthma, chronic obstructive pulmonary disease, etc. Thus, the protein of the present invention is useful as a reagent for screening the compound or salts thereof capable of inhibiting the activities of the protein of the present invention.

That is, the present invention provides:

(1) a method for screening the compound capable of inhibiting the activities (e.g., an eosinophil-mediated chemotactic activity, etc.) of the protein of the present invention (hereinafter sometimes merely referred to as the inhibitor, which comprises using the protein of the present invention. More specifically, the present invention provides, e.g.:

(2) a method for screening the inhibitor, which comprises comparing (i) the case where an eosinophil is brought into contact with the protein of the present invention and (ii) the case where an eosinophil and a test compound are brought into contact with the protein of the present invention.

Specifically, in the screening method described above, the method is characterized by measuring, e.g., the eosinophil-mediated chemotactic activity of the protein of the present invention in the cases (i) and (ii), and comparing them.

As the eosinophil, there is employed, e.g., mouse eosinophil, which can be prepared by a publicly known method described in, e.g., J. Leukocyte Biol., 60, 573 (1996), or by a modification thereof.

Examples of the test compound are a peptide, a protein, a non-peptide compound, a synthetic compound, a fermentation product, a cell extract, a plant extract, an animal tissue extract, and the like. These compounds may be novel compounds or publicly known compounds.

To perform the screening method described above, the protein of the present invention is suspended in a buffer suitable for screening to prepare a specimen for the protein of the present invention. Any buffer having pH of approximately 4 to 10 (desirably a pH of approximately 6 to 8) such as a phosphate buffer, Tris-hydrochloride buffer, etc. may be used, so long as it does not interfere the chemotactic reaction of eosinophils.

The eosinophil-mediated chemotactic activity of the protein of the present invention can be determined by a publicly known method described in, e.g., Immunity, 4, 1 (1996), or its modification.

For example, when a test compound increases the eosinophil-mediated chemotactic activity in the case (ii) described above by at least about 20%, preferably at least 30%, more preferably at least about 50%, as compared to the case of (i) above, the test compound can be screened to be a compound capable of inhibiting the eosinophil-mediated chemotactic activity of the protein of the present invention.

The compounds or salts thereof obtained using the screening methods or screening kits of the present invention are compounds screened from the test compounds described above, for example, peptides, proteins, non-peptide compounds, synthetic compounds, fermentation products, cell extracts, plant extracts, animal tissue extracts, blood plasma, etc., and are the compounds capable of inhibiting the activities (e.g., an eosinophil-mediated chemotactic activity, etc.) of the protein of the present invention.

As salts of these compounds, there may be employed the same salts as those of the protein I of the present invention described above.

The compound capable of inhibiting the activities of the protein of the present invention is useful as medicaments for the treatment/prevention of lung/chest diseases accompanied by inflammation of the lung/airways, including bronchial asthma, chronic obstructive pulmonary disease, etc.

When the compounds obtained using the screening methods or screening kits of the present invention are used as the therapeutic/prophylactic agents described above, they can be used in a conventional manner. The compounds may be used, for example, in the form of tablets, capsules, elixirs, microcapsules, a sterile solution, a suspension, etc., as in the pharmaceuticals containing the protein a of the present invention described above.

Since the thus obtained pharmaceutical preparation is safe and low toxic, the preparation can be administered to human or other warm-blooded animal (e.g., mouse, rat, rabbit, sheep, swine, bovine, horse, chicken, cat, dog, monkey, chimpanzee, etc.).

The dose of the compound or salts thereof varies depending on its action, target disease, subject to be administered, route for administration, etc.; when the compound capable of inhibiting the activity of the protein of the present invention is orally administered for the treatment of, e.g., bronchial asthma, the compound is normally administered in a dose of about 0.1 to about 100 mg, preferably about 1.0 to about 50 mg, and more preferably about 1.0 to about 20 mg per day for adult (as 60 kg body weight). In parenteral administration, a single dose of the compound varies depending on subject to be administered, target disease, etc. but it is advantageous for the treatment of bronchial asthma to administer the compound capable of inhibiting the activity of the protein of the present invention intravenously in the form of injection in a daily dose of about 0.01 to about 30 mg, preferably about 0.1 to about 20 mg, and more preferably about 0.1 to about 10 mg for adult (as 60 kg body weight). For other animal species, the corresponding dose as converted per 60 kg body weight can be administered.

(4) Quantification for the Protein a or Protein b of the Invention

The antibody to the protein of the present invention (hereinafter sometimes merely referred to as the antibody of the present invention) is capable of specifically recognizing the protein of the present invention, and can thus be used for a quantification of the protein of the present invention in a test sample fluid, in particular, for a quantification by sandwich immunoassay.

That is, the present invention provides:

(i) a method for quantification of the protein of the present invention in a test sample fluid, which comprises competitively reacting the antibody of the present invention, a test sample fluid and the labeled protein of the present invention, and measuring the ratio of the labeled protein of the present invention bound to said antibody; and, (ii) a method for quantification of the protein of the present invention in a test sample fluid, which comprises reacting the test sample fluid simultaneously or continuously with the antibody of the present invention immobilized on a carrier and another labeled antibody of the present invention, and then measuring the activity of the labeling agent on the insoluble carrier.

In the method (ii) for quantification described above, it is preferred that one antibody is capable of recognizing the N-terminal region of the protein of the present invention (preferably the protein I or protein II of the present invention), while another antibody is capable of recognizing the C-terminal region of the protein of the present invention (preferably the protein I or protein II of the present invention).

The monoclonal antibody to the protein of the present invention (hereinafter sometimes referred to as the monoclonal antibody of the invention) may be used to assay the protein of the present invention. Moreover, the protein can be detected by means of a tissue staining as well. For these purposes, the antibody molecule per se may be used or F(ab')$_2$, Fab' or Fab fractions of the antibody molecule may also be used.

There is no particular limitation to the method for quantification of the protein of the present invention using the antibody of the present invention; any method may be used, so far as it relates to a method, in which the amount of antibody, antigen or antibody-antigen complex can be detected by a chemical or physical means, depending on or corresponding to the amount of antigen (e.g., the amount of a protein) in a test sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of the labeling agent used in the assay method using the labeling substance are radioisotopes, enzymes, fluorescent substances, luminescent substances, and the like. Examples of the radioisotope are [$^{125}$I], [$^{131}$I], [$^{3}$H], [$^{14}$C], etc. Preferred examples of the enzyme are those that are stable and have a high specific activity, which include β-galactosidase, β-glucosidase, alkaline phosphatase, peroxidase, malate dehydrogenase, etc. Examples of the fluorescent substance are fluorescamine, fluorescein isothiocyanate, etc. Examples of the luminescent substance are luminol, a luminol derivative, luciferin, lucigenin, etc. Furthermore, the biotin-avidin system may also be used for binding of an antibody or antigen to a labeling agent.

In the immobilization of antigens or antibodies, physical adsorption may be used. Alternatively, chemical binding that is conventionally used for immobilization of proteins or enzymes may be used as well. Examples of the carrier include insoluble polysaccharides such as agarose, dextran and cellulose; synthetic resins such as polystyrene, polyacrylamide and silicone; glass; etc.

In the sandwich method, a test sample fluid is reacted with an immobilized monoclonal antibody of the present invention (first reaction), then reacted with another labeled monoclonal antibody of the present invention (second reaction) and the activity of the labeling agent on the insoluble carrier is assayed, whereby the amount of the protein of the present invention in the test sample fluid can be quantified. The first and second reactions may be carried out in a reversed order, simultaneously or sequentially with an interval. The type of the labeling agent and the method for immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the measurement sensitivity, etc.

In the method according to the present invention for assaying the protein of the present invention by the sandwich method, preferred monoclonal antibodies of the present invention used for the first and the second reactions are antibodies, which binding sites to the protein of the present invention are different from one another. That is, the antibodies used in the first and the second reactions are those wherein, when the antibody used in the second reaction recognizes the C-terminal region of the protein of the present invention, the antibody recognizing the site other than the C-terminal regions, e.g., recognizing the N-terminal region, is preferably used in the first reaction.

The monoclonal antibody of the present invention may be used in an assay system other than the sandwich method, such as a competitive method, an immunometric method, a nephrometry, etc.

In the competitive method, an antigen in a test sample fluid and a labeled antigen are competitively reacted with an antibody, then the unreacted labeled antigen (F) and the labeled antigen bound to the antibody (B) are separated (i.e., B/F separation) and the labeled amount of either B or F is measured to determine the amount of the antigen in the test sample fluid. In the reactions for such a method, there are a liquid phase method in which a soluble antibody is used as the antibody and the B/F separation is effected by polyethylene glycol while a second antibody to the antibody is used, and a solid phase method in which an immobilized antibody is used as the first antibody or a soluble antibody is used as the first antibody while an immobilized antibody. is used as the second antibody.

In the immunometric method, an antigen in a test sample fluid and an immobilized antigen are competitively reacted with a given amount of a labeled antibody followed by separating the solid phase from the liquid phase; or an antigen in a test sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the test sample fluid.

In the nephrometry, the amount of insoluble sediment, which is produced as a result of the antigen-antibody reaction in a gel or in a solution, is measured. Even when the amount of an antigen in a test sample fluid is small and only a small amount of the sediment is obtained, a laser nephrometry utilizing laser scattering can be suitably used.

In applying each of those immunoassays to the assay method for the present invention, any special conditions or operations are not required to set forth. The assay system for the protein of the present invention may be constructed in addition to conditions or operations conventionally used for each of the methods, taking the technical consideration of one skilled in the art into account consideration. For the details of such conventional technical means, a variety of reviews, reference books, etc. may be referred to.

For example, there are Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (published by Academic Press); etc.)

As described above, the protein of the present invention can be quantified with high sensitivity, using the antibody of the present invention.

Furthermore, (1) when an increased level of the protein of the present invention is detected by quantifying the level of the protein of the present invention using the antibody of the present invention, it can be diagnosed that one suffers from diseases such as lung/chest diseases accompanied by inflammation of the lung/airways, including bronchial asthma, chronic obstructive pulmonary disease, etc., or it is highly likely to suffer from these disease in the future.

The antibody of the present invention can be employed for detecting the protein of the present invention, which is present in a test sample fluid such as a body fluid, a tissue, etc. The antibody can also be used to prepare an antibody column for purification of the protein of the present invention, detect the protein of the present invention in each fraction upon purification, and analyze the behavior of the protein of the present invention in the cells under investigation.

(5) Gene Diagnostic Agent

By using the DNA of the present invention, e.g., as a probe, an abnormality (gene abnormality) of the DNA or mRNA encoding the protein of the present invention in human or warm-blooded animal (e.g., rat, mouse, guinea pig, rabbit, chicken, sheep, swine, bovine, horse, cat, dog, monkey, chimpanzee, etc.) can be detected. Therefore, the DNA of the present invention is useful as a gene diagnostic agent for detecting damages to the DNA or mRNA, its mutation, or decreased expression, increased expression, over expression, etc. of the DNA or mRNA.

The gene diagnosis described above using the DNA of the present invention can be performed by, for example, the publicly known Northern hybridization assay or the PCR-SSCP assay (Genomics, 5, 874–879 (1989); Proceedings of the National Academy of Sciences of the United States of America, 86, 2766–2770 (1989)), etc.

In case that overexpression is detected by, e.g., the Northern hybridization or DNA mutation is detected by the PCR-SSCP assay, it can be diagnosed that it is highly likely to suffer from diseases such as lung/chest diseases accompanied by inflammation of the lung/airways including bronchial asthma, chronic obstructive pulmonary disease, etc.

(6) Pharmaceutical Comprising an Antisense DNA

An antisense DNA that binds to the DNA of the present invention complementarily to suppress expression of the DNA can be used as the agent for the treatment/prevention of diseases such as lung/chest diseases accompanied by inflammation of the lung/airways including bronchial asthma, chronic obstructive pulmonary disease, etc., since the antisense DNA can suppress production of the protein of the present invention in vivo.

In the case that the antisense DNA described above is used as the therapeutic/prophylactic agent, the therapeutic/prophylactic agents for various diseases described above comprising the DNA of the present invention apply similarly to the antisense DNA.

For example, when the antisense DNA is used, the antisense DNA is administered directly, or the antisense DNA is inserted into an appropriate vector such as retrovirus vector, adenovirus vector, adenovirus-associated virus vector, etc., followed by treating in a conventional manner. The antisense DNA may be administered as it stands, or with a physiologically acceptable carrier to assist its uptake by gene gun or through a catheter such as a catheter with a hydrogel. Alternatively, the antisense DNA may be prepared into an aerosol, which is locally administered into the trachea as an inhalant.

In addition, the antisense DNA may also be employed as an oligonucleotide probe for diagnosis to examine the presence of the DNA of the present invention in tissues or cells and states of its expression.

(7) Pharmaceutical Composition Comprising the Antibody of the Present Invention

The DNA of the present invention having an activity of neutralizing the protein of the present invention can be used as a medicament for diseases such as lung/chest diseases accompanied by inflammation of the lung/airways including bronchial asthma, chronic obstructive pulmonary disease, etc.

The aforesaid therapeutic/prophylactic agent containing the antibody of the invention for the diseases described above can be administered orally or parenterally to human or other warm-blooded animal (e.g., rat, rabbit, sheep, swine, bovine, cat, dog, monkey, etc.), in its liquid form as it stands, or as a pharmaceutical composition in a suitable preparation form. The dose varies depending on subject to be administered, target disease, condition, route for administration, etc.; when the agent is administered to adult for the treatment/prevention of, e.g., bronchial asthma, the antibody of the present invention is normally advantageously administered intravenously, about 1to about 1 times a day, preferably about 1 to 3 times a day, in a single dose of about 0.01 to about 20 mg/kg body weight, preferably about 0.1 to about 10 mg/kg body weight, and more preferably about 0.1 to about 5 mg/kg body weight for adult. For other parenteral administration and oral administration, the dose corresponding to the dose above can be administered; when the condition is especially severe, the dose may be increased accordingly to the condition.

The antibody of the present invention may be administered in itself or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or an excipient conventionally used in the field of pharmaceutical preparations. Examples of the vehicle or excipient for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections, etc. Such injections are prepared by publicly known methods, e.g., by dissolving, suspending or emulsifying the aforesaid antibody or its salts in a sterile aqueous or oily liquid medium. For the aqueous medium for injection, for example, physiological saline and isotonic solutions containing glucose and other adjuvant, etc. are used. Appropriate dissolution aids, for example, alcohol (e.g., ethanol), polyalcohol (e.g., propylene glycol, polyethylene glycol), nonionic surfactant (e.g., polysorbate 80™, HCO-50 (polyoxyethylene (50 mol) adduct of hydrogenated castor oil)) may be used in combination. For the oily solution, for example, sesame oil, soybean oil and the like are used, and dissolution aids such as benzyl benzoate and benzyl alcohol may be used in combination. The thus-prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of 5 to 500 mg per unit dosage form, 5 to 100 mg especially for injections and 10 to 250 mg for other preparations.

Each composition described above may further contain other active components unless formulation with the antibody causes any adverse interaction.

(8) DNA Transgenic Animal

The present invention provides a non-human mammal bearing DNA encoding the protein of the present invention, which is exogenous (hereinafter abbreviated as the exogenous DNA of the present invention) or its variant DNA (sometimes simply referred to as the exogenous variant DNA of the present invention).

Thus, the present invention provides:

(1) a non-human mammal bearing the exogenous DNA of the present invention or its variant DNA;

(2) the mammal according to (1), wherein the non-human mammal is a rodent;

(3) the mammal according to (2), wherein the rodent is mouse or rat; and, (4) a recombinant vector bearing the exogenous DNA of the present invention or its variant DNA and capable of expressing in a mammal.

The non-human mammal bearing the exogenous DNA of the present invention or its variant DNA (hereinafter simply referred to as the DNA transgenic animal of the present invention) can be created by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method, etc. Also, it is possible to transfect the exogenous DNA of the present invention into a somatic cell, a living organ, a tissue cell, or the like by the DNA transfection methods, and utilize the transformant for cell culture, tissue culture, etc. In addition, these cells maybe fused with the above-described germinal cell by a publicly known cell fusion method to create the DNA transgenic animal of the present invention.

Examples of the non-human mammal that can be used include bovine, swine, sheep, goat, rabbits, dogs, cats, guinea pigs, hamsters, mice, rats, and the like. Above all, preferred are rodents, especially mice (e.g., C57Bl/6 strain, DBA2 strain, etc. for the pure line and for the cross line, B6C3F$_1$ strain, BDF$_1$ strain B6D2F$_1$ strain, BALB/c strain, ICR strain, etc.) or rats (e.g., Wistar, SD, etc.), since they are relatively short in ontogeny and life cycle from a standpoint of creating model animals for human disease.

"Mammals" in a recombinant vector that can be expressed in the mammals include the aforesaid non-human mammals and human.

The exogenous DNA of the present invention refers to the DNA of the present invention that is once isolated and extracted from mammals, not the DNA of the present invention inherently possessed by the non-human mammals.

The variant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean a DNA that expresses the abnormal protein of the present invention and exemplified by a DNA that expresses a protein to suppress the functions of the normal protein of the present invention.

The exogenous DNA of the present invention may be any one of those derived from a mammal of the same species as, or a different species from, the mammal as the target animal. In transfecting the DNA of the present invention, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the protein of the present invention, there are $Escherichia\ coli$-derived plasmids, $Bacillus\ subtilis$-derived plasmids, yeast-derived plasmids, bacteriophages such as $\lambda$ phage, retroviruses such as Moloney leukemia virus, etc., and animal viruses such as vaccinia virus, baculovirus, etc. Of these vectors, $Escherichia\ coli$-derived plasmids, $Bacillus\ subtilis$-derived plasmids, or yeast-derived plasmids, etc. are preferably used.

Examples of these promoters for regulating the DNA expression described above include 1) promoters for DNA derived from viruses (e.g., simian virus, cytomegalovirus, Moloney leukemia virus, JC virus, breast cancer virus, poliovirus, etc.), and 2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor $\beta$, keratins K1, K10 and K14, collagen types I and II, cyclic AMP-dependent protein kinase $\beta$I subunit, dystrophin, tartarate-resistant alkaline phosphatase, atrial natriuretic factor, endothelial receptor tyrosine kinase (generally abbreviated as Tie2), sodium-potassium adenosine triphosphorylase (Na, K-ATPase), neurofilament light chain, metallothioneins I and IIA, metalloproteinase I tissue inhibitor, MHC class I antigen (H-2L), H-ras, renin, dopamine $\beta$-hydroxylase, thyroid peroxidase (TPO), polypeptide chain elongation factor $1\alpha$ (EF-$1\alpha$), $\beta$ actin, $\alpha$ and $\beta$ myosin heavy chains, myosin light chains 1 and 2, myelin base protein, thyroglobulins, Thy-1, immunoglobulins, H-chain variable region (VNP), serum amyloid component P, myoglobin, troponin C, smooth muscle $\alpha$ actin, preproencephalin A, vasopressin, etc. Among them, cytomegalovirus promoters, human polypeptide elongation factor $1\alpha$ (EF-$1\alpha$) promoters, human and chicken $\beta$ actin promoters, etc., which protein can highly express in the whole body are preferred.

It is preferred that the vectors described above have a sequence for terminating the transcription of the desired messenger RNA in the DNA transgenic animal (generally termed terminator); for example, a sequence of each DNA derived from viruses and various mammals. SV40 terminator of the simian virus, etc. are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter region and the translational region, or at the 3' downstream of the translational region, depending upon purposes.

The translational region for the normal protein of the present invention can be obtained using as a starting material the entire genomic DNA or its portion of liver, kidney, thyroid cell or fibroblast origin from human or various mammals (e.g., rabbits, dogs, cats, guinea pigs, hamsters, rats, mice, etc.) or of various commercially available genomic DNA libraries, or using complementary DNA prepared by a publicly known method from RNA of liver, kidney, thyroid cell or fibroblast origin as a starting material. Also, an exogenous abnormal DNA can be obtained using complementary DNA prepared by a publicly known method from RNA of human fibroblast origin as a starting material. Alternatively, the translational region for a normal protein translational region obtained by the cell or tissue described above can be made variant by point mutagenesis.

The translational region can be prepared by a conventional genetic engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA of the present invention in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the exogenous DNA of the present invention is excessively present in all of the germinal cells and somatic cells thereof. The offspring of the animal that inherits the exogenous DNA of the present invention have excessively the DNA of the present invention in all of the germinal cells and somatic cells thereof.

By obtaining a homozygotic animal having the transfected DNA in both of homologous chromosomes and mating a male and female of the animal, all offspring can be passaged to retain the DNA.

In a non-human mammal bearing the normal DNA of the present invention, the normal DNA of the present invention has expressed to a high level, and may eventually develop the accentuated function of the protein of the present invention by promoting the function of endogenous normal DNA. Therefore, the animal can be utilized as a pathologic model animal for such a disease. For example, using the normal DNA transgenic animal of the present invention, it is possible to elucidate the mechanism of the accentuated function of the protein of the present invention and the pathological mechanism of the disease associated with the protein of the present invention and to determine how to treat the disease.

Furthermore, since a mammal transfected the exogenous normal DNA of the present invention exhibits a symptom of increasing the protein of the present invention liberated, the animal is usable for screening the therapeutic agent for the disease associated with the protein of the present invention.

On the other hand, non-human mammal having the exogenous abnormal DNA of the present invention can be passaged under normal breeding conditions as the DNA-bearing animal by confirming the stable retaining of the exogenous DNA via crossing. Furthermore, the desired exogenous DNA can be utilized as a starting material by inserting the DNA into the plasmid described above. The DNA construct with a promoter can be prepared by conventional genetic engineering techniques. The transfection of the abnormal DNA of the present invention at the fertilized egg cell stage is preserved to be present in all of the germinal and somatic cells of the mammals to be subjected. The fact that the abnormal DNA of the present invention is present in the germinal cells of the animal after DNA transfection means that all of the offspring of the prepared animal have the abnormal DNA of the present invention in all of the germinal and somatic cells. Such an offspring passaged the exogenous DNA of the present invention contains the abnormal DNA of the present invention in all of the germinal and somatic cells. A homozygous animal having the introduced DNA on both of homologous chromosomes can be acquired and then by mating these male and female animals, all the offspring can be bled to have the DNA.

Since non-human mammal having the abnormal DNA of the present invention may express the abnormal DNA of the present invention at a high level, the animal may be the function inactivation type in adaptability of the protein of the present invention by inhibiting the function of the endogenous normal DNA and can be utilized as its disease model animal. For example, using the abnormal DNA-transgenic animal of the present invention, it is possible to elucidate the mechanism of in adaptability of the protein of the present invention and to perform to study a method for treatment of this disease.

More specifically, the transgenic animal expressing the abnormal DNA of the present invention to a high level is also expected to serve as an experimental model for the elucidation of the mechanism of the functional inhibition (dominant negative effect) of normal protein by the abnormal protein of the present invention in the function inactive type in adaptability of the protein of the present invention.

A mammal bearing the abnormal exogenous DNA of the present invention is also expected to serve for screening a candidate drug for the treatment of the function inactive type in adaptability of the protein of the present invention, since the protein of the present invention is increased in such an animal in its free form.

Other potential applications of two kinds of the transgenic animals described above include:

1) use as a cell source for tissue culture;
2) elucidation of the relation to a protein that is specifically expressed or activated by the protein of the present invention, by direct analysis of DNA or RNA in tissue of the DNA transgenic animal of the present invention or by analysis of the protein tissue expressed by the DNA;
3) research in the function of cells derived from tissues that are cultured usually only with difficulty, using cells of tissue bearing the DNA cultured by a standard tissue culture technique;
4) screening of a drug that enhances the functions of cells using the cells described in 3) above; and,
5) isolation and purification of the variant protein of the present invention and preparation of an antibody thereto.

Furthermore, clinical conditions of a disease associated wit the protein of the present invention, including the function inactive type in adaptability of the protein of the present invention can be determined using the DNA transgenic animal of the present invention. Also, pathological findings on each organ in a disease model associated with the protein of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and degrading with a proteinase such as trypsin, etc., followed by establishing the line of culturing or cultured cells. Furthermore, the DNA transgenic animal of the present invention can serve as identification of cells capable of producing the protein of the present invention, and as studies on association with apoptosis, differentiation or propagation or on the mechanism of signal transduction in these properties to inspect any abnormality therein. Thus the DNA transgenic animal of the present invention can provide an effective research material for the protein of the present invention and for elucidating the function and effect thereof.

To develop a drug for the treatment of diseases associated with the protein of the present invention, including the function inactive type in adaptability of the protein of the present invention, using the DNA transgenic animal of the present invention, an effective and rapid method for screening can be provided by using the method for inspection and the method for quantification, etc. described above. It is also possible to investigate and develop a method for DNA therapy for the treatment of diseases associated with the protein of the present invention, using the DNA transgenic animal of the present invention or a vector capable of expressing the exogenous DNA of the present invention.

(9) Knockout Animal

The present invention provides a non-human mammal embryonic stem cell bearing the DNA of the present invention inactivated and a non-human mammal deficient in expressing the DNA of the present invention.

Thus, the present invention provides:

(1) a non-human embryonic stem cell, in which the DNA of the present invention is inactivated;

(2) an embryonic stem cell according to (1), wherein the DNA is inactivated by introducing a reporter gene (e.g., β-galactosidase gene derived from *Escherichia coli*);

(3) an embryonic stem cell according to (1), which is resistant to neomycin;

(4) an embryonic stem cell according to (1), wherein the non-human mammal is a rodent;

(5) an embryonic stem cell according to (4), wherein the rodent is mouse;

(6) a non-human mammal deficient in expressing the DNA of the present invention, wherein the DNA is inactivated;

(7) a non-human mammal according to (6), wherein the DNA is inactivated by inserting a reporter gene (e.g., β-galactosidase derived from *Escherichia coli*) therein and the reporter gene is capable of being expressed under control of a promoter for the DNA of the present invention;

(8) a non-human mammal according to (6), wherein the non-human mammal is a rodent;

(9) a non-human mammal according to (8), wherein the rodent is mouse; and,

(10) a method for screening a compound capable of promoting or inhibiting the promoter activity for the DNA of the present invention, which comprises administering a test compound to the mammal of (7) and detecting expression of the reporter gene.

The non-human mammal embryonic stem cell, in which the DNA of the present invention is inactivated, refers to a non-human mammal embryonic stem cell that suppresses the ability of the non-human mammal to express the DNA by artificially mutating the DNA of the present invention, or the DNA has no substantial ability to express the protein of the present invention (hereinafter sometimes referred to as the knockout DNA of the present invention) by substantially inactivating the activities of the protein of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention that the desired non-human mammal possesses, inserting a DNA fragment having a DNA sequence constructed by inserting a drug resistant gene such as a neomycin resistant gene or a hygromycin resistant gene, or a reporter gene such as lacZ (β-galactosidase gene) or cat (chloramphenicol acetyltransferase gene), etc. into its exon site thereby to disable the functions of exon, or integrating to a chromosome of the subject animal by, e.g., homologous recombination, a DNA sequence which terminates gene transcription (e.g., poly A additional signal, etc.) in the intron between exons thus to inhibit the synthesis of complete messenger RNA and eventually destroy the gene (hereinafter simply referred to as targeting vector). The thus obtained ES cells is subjected to Southern hybridization analysis with a DNA sequence on or near the DNA of the present invention as a probe, or to PCR analysis with a DNA sequence on the targeting vector and another DNA sequence near the DNA of the present invention, which is not included in the targeting vector as primers, to select the knockout ES cell of the present invention.

The parent ES cells to inactivate the DNA of the present invention by homologous recombination, etc. may be of a strain already established as described above, or may be originally established in accordance with a modification of the known method by Evans and Kaufman supra. For example, in the case of mouse ES cells, currently it is common practice to use ES cells of the 129 strain. However, since their immunological background is obscure, the C57BL/6 mouse or the $BDF_1$ mouse (F1 hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by back-crossing with the C57BL/6 mouse, since its background is of the C57BL/6 mouse, as well as being advantageous in that ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is also desirable that sexes be identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Second selection can be achieved by, for example, number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability. For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LIF (1 to 10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 days; it is desirable that cells be observed at passage and cells found to be morphologically abnormal in culture, if any, be abandoned.

Where ES cells are allowed to reach a high density in mono-layers or to form cell aggregates in suspension under appropriate conditions, they will spontaneously differentiate to various cell types, for example, pariental and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtainable from the differentiated ES cells of the present invention are useful for studying the functions of the protein of the present invention cytologically.

The non-human mammal deficient in expression of the DNA of the present invention can be identified from a normal animal by measuring the mRNA amount in the subject animal by a publicly known method, and indirectly comparing the degrees of expression.

As the non-human mammal, the same examples supra apply.

With respect to the non-human mammal deficient in expression of the DNA of the present invention, the DNA of the present invention can be made knockout by transfecting a targeting vector, prepared as described above, to non-human mammal embryonic stem cells or oocytes thereof, and conducting homologous recombination in which a targeting vector DNA sequence, wherein the DNA of the present invention is inactivated by the transfection, is replaced with the DNA of the present invention on a chromosome of a non-human mammal embryonic stem cell or embryo thereof.

The knockout cells with the DNA of the present invention disrupted can be identified by Southern hybridization analysis with a DNA fragment on or near the DNA of the present invention as a probe, or by PCR analysis using a DNA sequence on the targeting vector and another DNA sequence which is not included in the targeting vector as primers. When non-human mammalian embryonic stem cells are used, a cell line wherein the DNA of the present invention is inactivated by homologous recombination is cloned; the resulting cloned cell line is injected to, e.g., a non-human mammalian embryo or blastocyte, at an appropriate stage such as the 8-cell stage. The resulting chimeric embryos are transplanted to the uterus of the pseudopregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the protein of the present invention. The individuals deficient in homozygous expression of the protein of the present invention can be obtained from offspring of the intercross between the heterozygotes.

When an oocyte or egg cell is used, a DNA solution may be injected, e.g., to the prenucleus by microinjection thereby to obtain a transgenic non-human mammal having a targeting vector introduced in a chromosome thereof. From such transgenic non-human mammals, those having a mutation at the locus of the DNA of the present invention can be obtained by selection based on homologous recombination.

As described above, individuals, in which the DNA of the present invention is rendered knockout, permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell in which the DNA of the present invention is inactivated is very useful for preparing a non-human mammal deficient in expression of the DNA of the present invention.

Since the non-human mammal, in which the DNA of the present invention is inactivated, lacks various biological activities derived from the protein of the present invention, such an animal can be a disease model suspected of inactivated biological activities of the protein of the present invention and thus, offers an effective study to investigate causes for and therapy for these diseases.

(10) Method for Screening of a Compound Having the Therapeutic/Prophylactic Effects for Diseases Caused by Deficiency, Damages, etc. of the DNA of the Present Invention The non-human mammal deficient in expression of the DNA of the present invention can be employed for screening of a compound having the therapeutic/prophylactic effects for diseases (e.g., infectious diseases, etc.) caused by deficiency, damages, etc. of the DNA of the present invention.

That is, the present invention provides a method for screening of a compound having the therapeutic/prophylactic effects for diseases caused by deficiency, damages, etc. of the DNA of the present invention, which comprises administering a test compound to the non-human mammal deficient in expression of the DNA of the present invention and observing and measuring a change occurred in the animal.

As the non-human mammal deficient in expression of the DNA of the present invention, which can be employed for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma, and the like and these compounds may be novel compounds or publicly known compounds.

Specifically, the non-human mammal deficient in expression of the DNA of the present invention is treated with a test compound, comparison is made with an intact animal for control and a change in each organ, tissue, disease conditions, etc. of the animal is used as an index to assess the therapeutic/prophylactic effects of the test compound.

For treating an animal to be test with a test compound, for example, oral administration, intravenous injection, etc. are applied and the treatment is appropriately selected depending upon conditions of the test animal, properties of the test compound, etc. Furthermore, an amount of a test compound to be administered can be selected depending on the route for administration, nature of the test compound, and the like.

For example, when a compound having the therapeutic/prophylactic effects against bronchial asthma is screened, the non-human mammal deficient in expression of the DNA of the present invention is subjected to immunization with an antigen (e.g., OVA) followed by inhalation of the same antigen (e.g., OVA) for airway hyperresponsiveness, the test compound is administered to the animal and, airway resistance, eosinophil infiltration, etc. of the animal is measured with passage of time.

In the screening method supra, when a test compound is administered to an animal to be tested and found to inhibit an increase in the airway resistance of the test animal by the antigen inhalation by at least about 10%, preferably at least about 30% and more preferably at least about 50%, the test compound can be screened to be a compound having a therapeutic and prophylactic effect for bronchial asthma.

The compound obtainable using the above screening method is a compound screened from the test compounds described above and exhibits the therapeutic and prophylactic effect for diseases (e.g., bronchial asthma, etc.) caused by an increased expression, etc. of the protein of the present invention. Therefore, the compound can be employed as a safe and low toxic drug for the treatment/prevention of these diseases. Furthermore, compounds derived from such a compound obtainable by the screening supra can be similarly employed.

The compound obtained by the screening above may be used in the form of salts with physiologically acceptable acids (e.g., inorganic acids or organic acids) or bases (e.g., alkali metal salts), preferably in the form of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

A pharmaceutical comprising the compound obtained by the above screening method or salts thereof may be manufactured in a manner similar to the method for preparing the pharmaceutical comprising the protein of the present invention described here in above. Since the pharmaceutical composition thus obtained is safe and low toxic, it can be administered to human and another mammal (e.g., rat, mouse, guinea pig, rabbit, sheep, swine, bovine, horse, cat, dog, monkey, etc.).

Although the dose of the compound or its salt to be administered varies depending upon target disease, subject to be administered, route of administration, etc., in general, for oral administration to an adult (as 60 kg body weight) for the treatment of, e.g., bronchial asthma, the compound is administered in a daily dose of about 0.1 to about 100 mg, preferably about 1.0 to about 50 mg, more preferably about 1.0 to about 20 mg. For parenteral administration to an adult (as 60 kg body weight) for the treatment of, e.g., bronchial asthma, it is advantageous to administer the composition intravenously in the form of an injectable preparation in a single dose of about 0.01 to about 30 mg, preferably about 0.1 to about 20 mg, more preferably about 0.1 to about 10 mg, though the single dosage varies depending upon particular subject, particular disease, etc. As for other animals, the composition can be administered in the above dosage with converting it into that for the body weight of 60 kg.

(11) Method for Screening a Compound Capable of Promoting or Inhibiting the Activities of a Promoter to the DNA of the Present Invention The present invention provides a method for screening a compound or salts thereof capable of promoting or inhibiting the activities of a promoter to the DNA of the present invention, which comprises administering a test compound to a non-human mammal deficient in expression of the DNA of the present invention and detecting expression of the reporter gene.

In the screening method supra, the non-human mammal deficient in expression of the DNA of the present invention is employed, in the aforesaid non-human mammal deficient in expression of the DNA of the present invention, as an animal in which the DNA of the present invention is inactivated by introducing a reporter gene and the reporter gene is expressed under control of a promoter to the DNA of the present invention.

The same examples of the test compound apply to specific compounds used for the screening.

As the reporter gene, the same specific examples apply to this screening method. Preferably employed are β-galactosidase (lacZ), soluble alkaline phosphatase gene, luciferase gene, and the like.

Since a reporter gene is present under control of a promoter to the DNA of the present invention in the non-human mammal deficient in expression of the DNA of the present invention, wherein the DNA of the present invention is substituted with the reporter gene, the activity of the promoter can be detected by tracing expression of a substance encoded by the reporter gene.

When a part of the DNA region encoding the protein of the present invention is substituted with, e.g., β-galactosidase gene (lacZ) derived from *Escherichia coli*, β-galactosidase is expressed in a tissue where the protein of the present invention should originally be expressed, instead of the protein of the present invention. Thus, the state of expression of the protein of the present invention can be readily observed in vivo of an animal by staining with a reagent, e.g., 5-bromo-4-chloro-3-indolyl-β-galactopyranoside (X-gal) that is a substrate for β-galactosidase. Specifically, a mouse deficient in the protein of the present invention, or its tissue section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may be detected in a conventional manner.

The compound or salts thereof obtained using the screening method supra are compounds that are screened from the test compounds described above and capable of promoting or inhibiting the promoter activity to the DNA of the present invention.

The compound obtained by the screening method above may be used in the form of salts with physiologically acceptable acids (e.g., inorganic acids or organic acids) or bases (e.g., alkali metal salts), preferably in the form to of physiologically acceptable acid addition salts. Examples of such salts are salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The compounds or salts thereof capable of promoting the promoter activity to the DNAa of the present invention can promote expression of the protein a of the present invention thereby to promote the activities of the protein, and are thus useful as safe and low toxic medicaments for the treatment/prevention of diseases such as infectious diseases (e.g., HIV infection, HBV infection, HCV infection, tuberculosis infection, opportunistic infection, etc.), and the like.

On the other hand, the compounds or salts thereof capable of inhibiting the promoter activity to the DNAa or DNAb of the present invention can inhibit expression of the protein of the present invention thereby to inhibit the activities of the protein, and are thus useful as safe and low toxic medicaments for diseases such as lung/chest diseases accompanied by inflammation of the lung/airways, including bronchial asthma, chronic obstructive pulmonary disease, etc.

Compounds derived from the compounds obtained by the screening above may also be used similarly.

The pharmaceutical comprising the compounds or salts thereof obtained by the screening method may be manufactured similarly to the pharmaceuticals comprising the protein of the present invention described above.

Since the pharmaceutical composition thus obtained is safe and low toxic, it can be administered to human or another mammal (e.g., rat, mouse, guineapig, rabbit, sheep, swine, bovine, horse, cat, dog, monkey, etc.).

The dose of the compound or salts thereof varies depending on target disease, subject to be administered, method for administration, etc.; for example, when the compound capable of inhibiting the promoter activity to the DNA of the present invention is orally administered for the treatment of, e.g., bronchial asthma, the dose is normally about 0.1 to about 100 mg, preferably about 1.0 to about 50 mg, more preferably about 1.0 to about 20 mg per day for adult (as 60 kg body weight). In parenteral administration for the treatment of, e.g., bronchial asthma, the single dose varies depending on subject to be administered, target disease, etc. but it is advantageous to administer, for example, the compound capable of inhibiting the promoter activity to the DNA of the present invention intravenously at a daily dose of about 0.01 to about 30 mg, preferably about 0.1 to about 20 mg, more preferably about 0.1 to about 10 mg for adult (as 60 kg body weight). For other animal species, the corresponding dose as converted per 60 kg weight can be administered.

On the other hand, when the compound capable of promoting the promoter activity to the DNAa of the present invention is orally administered for the treatment of, e.g., infectious diseases, the dose is normally about 0.1 to about 100 mg, preferably about 1.0 to about 50 mg, more preferably about 1.0 to about 20 mg per day for adult (as 60 kg body weight). In parenteral administration for the treatment of, e.g., infectious diseases, the single dose varies depending on subject to be administered, target disease, etc. When the compound capable of inhibiting the promoter activity to the DNA of the present invention is administered to an adult (as 60 kg body weight) generally in the form of injection, it is advantageous to administer the compound intravenously at a daily dose of about 0.01 to about 30 mg, preferably about 0.1 to about 20 mg, more preferably about 0.1 to about 10 mg. For other animal species, the corresponding dose as converted per 60 kg weight can be administered.

As stated above, the non-human mammal deficient in expression of the DNA of the present invention is extremely useful for screening the compound or its salt capable of promoting or inhibiting the activity of a promoter to the DNA of the present invention and can greatly contribute to the elucidation of causes for various diseases suspected of deficiency in expression of the DNA of the present invention and for the development of prophylactic/therapeutic agent for these diseases.

Furthermore, a so-called transgenic animal (gene transferred animal) can be prepared by using a DNA containing a promoter region of the protein of the present invention, ligating genes encoding various proteins downstream and injecting the same into oocyte of an animal. It is then possible to synthesize the protein therein specifically and study its activity in vivo. When an appropriate reporter gene is ligated to the promoter site above and a cell line that express the gene is established, the resulting system can be utilized for exploring a low molecular compound having the action of specifically promoting or inhibiting the in vivo productivity of the protein of the present invention, per se. Further analysis of the promoter region enables to find a new cis-element or a transcription factor bound thereto.

In the specifications and drawings, the codes of bases and amino acids are denoted in accordance with the IUPAC-IUB Commission on Biochemical Nomenclature or by the common codes in the art, examples of which are shown below. For amino acids that may have the optical isomer, L form is presented unless otherwise indicated.

| | |
|---|---|
| DNA | deoxyribonucleic acid |
| cDNA | complementary deoxyribonucleic acid |
| A | adenine |
| T | thymine |
| G | guanine |
| C | cytosine |
| RNA | ribonucleic acid |
| mRNA | messenger ribonucleic acid |
| dATP | deoxyadenosine triphosphate |
| dTTP | deoxythymidine triphosphate |
| dGTP | deoxyguanosine triphosphate |
| dCTP | deoxycytidine triphosphate |
| ATP | adenosine triphosphate |
| EDTA | ethylenediaminetetraacetic acid |
| SDS | sodium dodecyl sulfate |
| Gly | glycine |
| Ala | alanine |
| Val | valine |
| Leu | leucine |
| Ile | isoleucine |
| Ser | serine |
| Thr | threonine |
| Cys | cysteine |
| Met | methionine |
| Glu | glutamic acid |
| Asp | aspartic acid |
| Lys | lysine |
| Arg | arginine |
| His | histidine |
| Phe | phenylalanine |
| Tyr | tyrosine |
| Trp | tryptophan |
| Pro | proline |
| Asn | asparagine |
| Gln | glutamine |
| pGlu | pyroglutamic acid |

Substituents, protecting groups, and reagents used in this specification are presented as the codes below.

| | |
|---|---|
| Me | methyl group |
| Et | ethyl group |
| Bu | butyl group |
| Ph | phenyl group |
| TC | thiazolidine-4(R)-carboxamide group |
| Tos | p-toluenesulfonyl |
| CHO | formyl |
| Bzl | benzyl |
| Cl$_2$Bzl | 2,6-dichlorobenzyl |
| Bom | benzyloxymethyl |
| Z | benzyloxycarbonyl |
| Cl–Z | 2-chlorobenzyl oxycarbonyl |
| Br–Z | 2-bromobenzyl oxycarbonyl |
| Boc | t-butoxycarbonyl |
| DNP | dinitrophenol |
| Trt | trityl |
| Bum | t-butoxymethyl |
| Fmoc | N-9-fluorenyl methoxycarbonyl |
| HOBt | 1-hydroxybenztriazole |
| HOOBt | 3,4-dihydro-3-hydroxy-4-oxo-1,2,3-benzotriazine |
| HONB | 1-hydroxy-5-norbornene-2,3-dicarboxyimide |
| DCC | N,N'-dichlorohexylcarbodiimide |

The sequence identification numbers in the sequence listing of the specification indicate the following sequences.
[SEQ ID NO:1]

This shows the amino acid sequence of the (mature) protein of the present invention derived from human stomach.

[SEQ ID NO:2]

This shows the amino acid sequence of the signal peptide of the invention.

[SEQ ID NO:3]

This shows the base sequence of DNA encoding the human stomach-derived the (mature) protein of the present invention having the amino acid sequence represented by SEQ ID NO:1.

[SEQ ID NO:4]

This shows the base sequence of DNA encoding the signal peptide of the present invention having the amino acid sequence represented by SEQ ID NO:2.

[SEQ ID NO:5]

This shows the amino acid sequence of the precursor protein of the human stomach-derived protein of the present invention.

[SEQ ID NO:6]

This shows the base sequence of primer PR1 used in EXAMPLE 1.

[SEQ ID NO:7]

This shows the base sequence of primer PR2 used in EXAMPLE 1.

[SEQ ID NO:8]

This shows the base sequence of primer PR3 used in EXAMPLES 1 and 4.

[SEQ ID NO:9]

This shows the base sequence of primer PR4 used in EXAMPLE 1.

[SEQ ID NO:10]

This shows the base sequence of primer PR5 used in EXAMPLE 1.

[SEQ ID NO:11]

This shows the base sequence of primer PR6 used in EXAMPLE 1.

[SEQ ID NO:12]

This shows the base sequence of primer PR7 used in EXAMPLE 1.

[SEQ ID NO:13]

This shows the base sequence of primer PR8 used in EXAMPLE 1.

[SEQ ID NO:14]

This shows the base sequence of cDNA containing ECF-L full-length gene acquired in EXAMPLE 1.

[SEQ ID NO:15]

This shows the base sequence of ECF-L gene probe used in EXAMPLE 2.

[SEQ ID NO:16]

This shows the base sequence of clone hECF-L-2 acquired in EXAMPLE 5.

[SEQ ID NO:17]

This shows the amino acid sequence of the protein encoding the ECF-L full-length gene acquired in EXAMPLE 1.

[SEQ ID NO:18]

This shows the amino acid sequence of ECF-L (mature) protein.

EXAMPLES

Hereinafter the present invention will be described in more detail with reference to EXAMPLES but is not deemed to be limited thereto. The gene manipulation procedures using *Escherichia coli* were performed according to the methods described in the Molecular Cloning.

*Escherichia coli* JM109/pT7-mECFL bearing the plasmid obtained in EXAMPLE 1 by cloning mouse ECF-L full-length DNA fragment to pT7 Blue-T Vector was on deposit with the Ministry of International Trade and Industry, Agency of Industrial Science and Technology, National Institute of Bioscience and Human Technology (NIBH) at 1-3, Higashi 1 chome, Tsukuba-shi, Ibaraki-ken, Japan (zip code 305-8566), as the Accession Number FERM BP-6881 on Sep. 20, 1999 and with Institute for Fermentation, Osaka (IFO) at 17-85, Juso honcho 2-chome, Yodogawa-ku, Osaka-shi, Japan (zipcode 532-8686), as the Accession Number IFO 16315 on Aug. 24, 1999.

*Escherichia coli* DH5α/pcDNA-hECFL bearing the plasmid pcDNA-hECFL obtained in EXAMPLE 6 was on deposit with NIBH as the Accession Number FERM BP-6878 on Sep. 20, 1999 and with IFO as the Accession Number IFO 16312 on Aug. 24, 1999.

Example 1

Cloning of ECF-L Gene Showing Increased Expression in Model Mouse with Increased Airway Hyperresponsiveness Model mice with increased airway hyperresponsiveness were prepared through sensitization by intraperitoneally injecting 400 μl of saline containing 200 μl of OVA (ovalbumin) and 2 mg of alum to BALB/c mice (male, 6 weeks old) and then boosting by intraperitoneal injection of 20 μg of saline containing 10 μg of OVA and 1 mg of alum to the animal one week after, followed by inhalation of 5% OVA solution dissolved in PBS of ½ concentration for 25 minutes under unanaesthetised and spontaneous respiration conditions over 7 consecutive days from one week after. The steroid group was prepared by intraperitoneally injecting 1 mg/kg of dexamethasone an hour before the OVA inhalation. Aerozollization was effected using a ultrasonic nebulizer (Soniclizer 305, ATOM Medical). Accentuation of airway hyperresponsiveness was determined by the Konzett-Rossler method in terms of bronchoconstriction induced by acetylcholine (62.5–2000 μg/kg) given 24 hours after the final antigen inhalation. Bronchoalveolar lavage fluid (BALF) was prepared, after death under pentobarbital anesthesia, by inserting a tracheal cannula into the animal and washing 3times with 0.5 ml of PBS. Next, a smear specimen was prepared using cytospin (700 rpm, 1 min.). After Diff-Quick staining and microscopic inspection, the proportion of macrophages, eosinophils, neutrophils, lymphocytes and other cells was calculated.

Poly (A)+RNA used as a sample was prepared by extracting the total RNA from the lung/bronchi of normal mice, the lung/bronchi of model mice with increased airway hyperresponsiveness and its dexamethasone group, using ISOGEN (manufactured by Wako Pure Chemical Industries, Ltd.), and then passing through oligo-dT cellulose column (manufactured by Pharmacia). Using 2 μg aliquot each of these poly (A)+RNAs as the starting material, cDNA fragments (fragments wherein a part of cDNA is amplified by PCR) specifically expressed in the lung/bronchi of model mice with increased airway hyperresponsiveness were collected by subtraction using PCR-select cDNA subtraction kit (manufactured by Clontech Laboratories, Inc.). The adaptor sequence for the subtraction added to the resulting PCR fragment at the both ends thereof was removed by digestion with restriction enzyme RsaI to change to the DNA fragment with blunt ends. The fragment was then subcloned to pT7 Blue T-Vector (manufactured by Novagen, Inc.). The DNA base sequence of the subcloned cDNA fragment was decoded, and based on the decoded base sequence, homology search was conducted by blast N using public Geneble database.

The result revealed that 10 out of 120 clones checked on all coincided with the base sequence encoding a known mouse ECF-L gene (GENEBANK ACCESSION NUMBER: D87757). So, cDNA was synthesized from poly(A)+ RNA in the lung of model mice with increased airway hyperresponsiveness, using cDNA synthesis kit (manufactured by Takara Shuzo Co., Ltd.). This cDNA was as a template and PCR was carried out using 2 primers of 5'-non-translational region (PR1: SEQ ID NO:6) and 3'-non-translational region(PR2: SEQ ID NO:7) of the ECF-L gene to acquire the ECF-L full-length gene (SEQ ID NO:14). Using Takara EX Taq (manufactured by Takara Shuzo Co., Ltd.), after incubation 98° C. for a minute, the reaction was carried out by repeating 30 cycles in Thermal Cycler Gene Amp PCR System 9700 (manufactured by Perkin-Elmer, Inc.), in which one cycle is set to include 98° C. for 10 seconds, 60° C. for 1 minute and then 72° C. for 3 minutes, and finally by reacting at 72° C. for 10 minutes. The resulting ECF-L full-length DNA fragment was cloned to pT7 Blue-T Vector. Using synthetic primers (PR1 to 8: SEQ ID NOs:6–13), cycle sequencing was conducted to confirm the base sequence of the product obtained by fluorescent DNA sequencer (ABI PRISM TM377, manufactured by Perkin-Elmer, Inc.).

Example 2
Analysis on Tissue Distribution on the ECF-L Gene in Model Mice with Increased Airway Hyperresponsiveness Each organ (lung, heart, liver, kidney, brain, thymus, spleen, small intestine, large intestine, stomach) was isolated from normal mice and model mice with increased airway hyperresponsiveness, and total RNAs were prepared therefrom, using ISOGEN (manufactured by Wako Pure Chemical Industries, Ltd.). The total RNAs were passed through oligo-dT cellulose column (manufactured by pharmacia, Inc.) to prepare poly(A)+RNAs. After 0.5 µg of this poly(A)+RNAs were electrophoresed on 1.1% agarose gel electrophoresis containing 2.2 M formalin, the RNAs were blotted to nylon membrane filters (Hybond-N+, made by Amersham Pharmacia Biotech, Inc.) by capillary blotting for 18 hours. The RNAs were fixed on the nylon membrane filters through UV treatment, followed by hybridization at 65° C. in Express Hyb Hybridization Solution (manufactured by Clontech Laboratories, Inc.). On the other hand, one of the ECF-L cDNA fragments shown as a probe in EXAMPLE 1 (SEQ ID NO:15) was labeled with $[\alpha\text{-}^{32}\text{P}]$ dCTP and Bca BEST Labeling Kit (manufactured by Takara Shuzo Co., Ltd.). Hybridization was carried out at 65° C. for 2 hours in Express Hyb Hybridization Solution. Filters were finally rinsed with 0.1×SSC in 0.1% SDS solution at 50° C. followed by detection using BAS-2000 (manufactured by Fuji Photo Film Co., Ltd.). As a result, expression of the ECF-L gene (mRNA) was observed in the lung, thymus and stomach in normal mice. In mice with increased airway hyperresponsiveness, the expression was markedly observed in the lung, indicating that the expression was strongly induced with increased airway hyperresponsiveness. An increase of expression was also noted in the thymus and stomach (FIG. 1).

Figure 2:
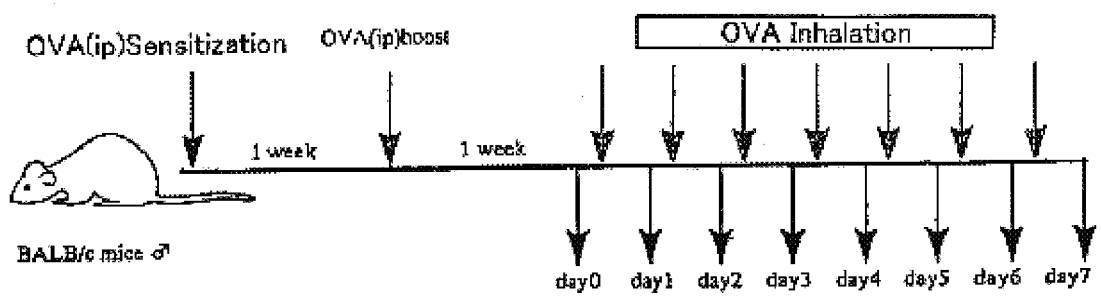
FIG. 2 shows administration schedule in the experiment described in EXAMPLE 3.
Figure 3:
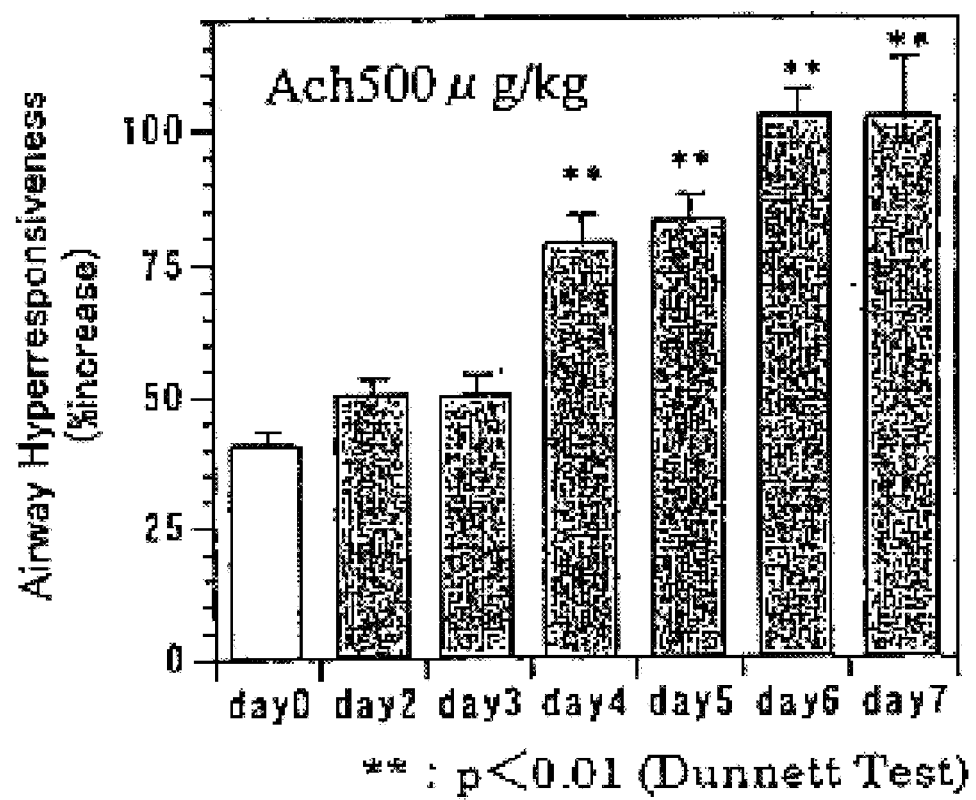
FIG. 3 shows change in airway reactivity with time course, by administration of acetylcholine in a dose of 500 μg/kg, wherein Ach is acetylcholine.
Figure 4:
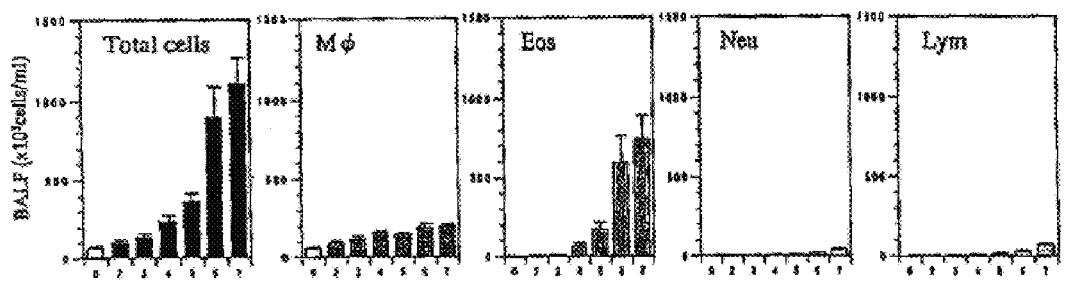
FIG. 4 shows change with time course in number of infiltrated cells in the alveolar lavage fluid shown in EXAMPLE 3, wherein Mφ, Eos, Neu and Lym designate macrophage, eosinophil, neutrophil and lymphocyte, respectively.
Figure 5:
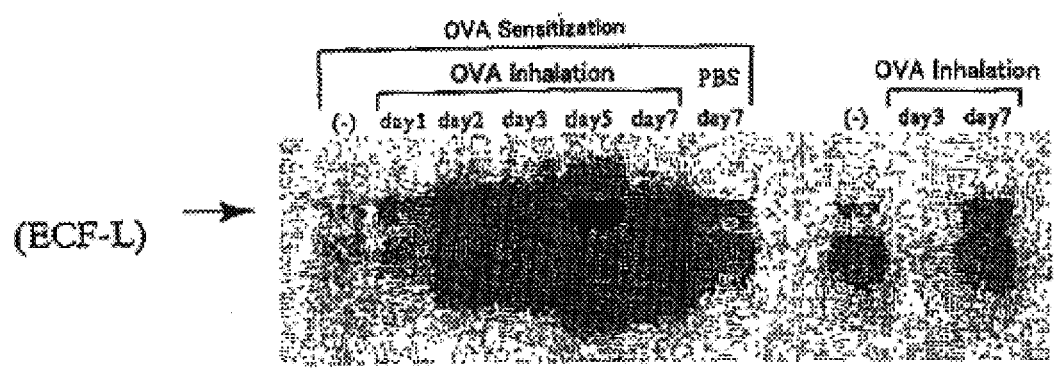
FIG. 5 shows change of ECF-L gene (mRNA) with time course in model mouse with increased airway hyperresponsiveness shown in EXAMPLE 3.

Example 3
Analysis on the ECF-L Gene with Passage of Time in Model Mice with Increased Airway Hyperresponsiveness Using the model mice with increased airway hyperresponsiveness explained in EXAMPLE 1 above, the increased airway hyperresponsiveness and the count of infiltrated cells into alveolar lavage fluids were measured before OVA inhalation and on Days 2, 3, 4, 5, 6 and 7 after OVA inhalation as in EXAMPLE 1 (FIGS. 2, 3 and 4). In addition, the lung before OVA inhalation and on Days 1, 2, 3, 5 and 7 after OVA inhalation was isolated, and subjected to Northern blotting analysis as in EXAMPLE 2 (FIG. 5). As a result, the increased airway hyperresponsiveness and infiltration of eosinophils into alveolar lavage fluids were induced on or after Day 4 after OVA inhalation, whereas expression of the ECF-L gene was markedly induced from Day 2 after OVA inhalation. That is, expression of the ECF-L gene occurred prior to the increased airway hyperresponsiveness and eosinophil infiltration, but the ECF-L gene was not expressed as the outcome of airway inflammation, suggesting the possibility that induction of the ECF-L gene expression would cause the increased airway hyperresponsiveness and eosinophil infiltration into alveolar lavage fluids.

Figure 6:
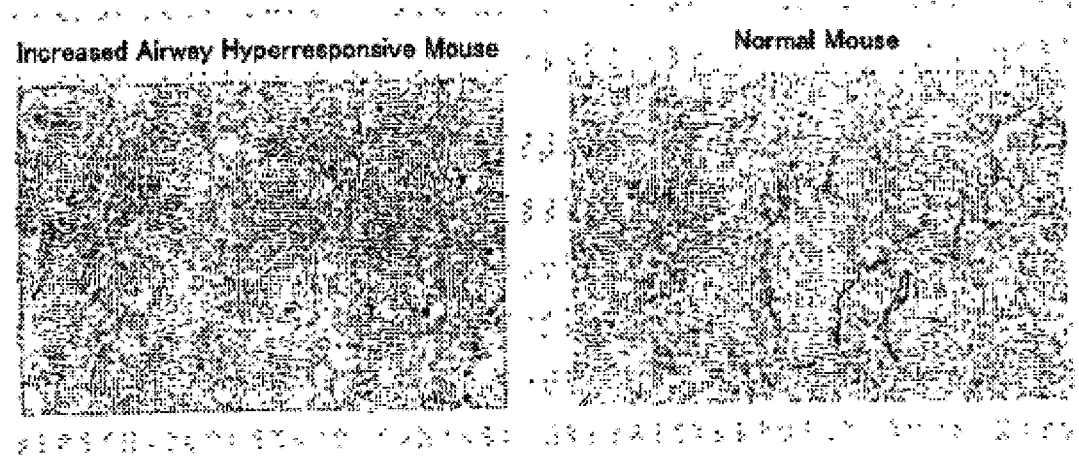
FIG. 6 indicates the expression site of ECF-L gene on frozen sections from model mouse with increased airway hyperresponsiveness and normal mouse, shown in EXAMPLE 4.

Example 4
Identification of the ECF-L Gene Expression Site in Model Mice with Increased Airway Hyperresponsiveness After perfusion in lung of normal mice and model mice with increased airway hyperresponsiveness and fixation with 4% paraformaldehyde, the lung was isolated and fixed at 4° C. overnight. Thereafter, a sucrose-HBSS solution was replaced to finally reach 18% sucrose-HBSS solution by gradually increasing the concentration of sucrose, and the lung was frozen in dry ice. After allowing to stand in a cryostat at −14° C. for 3 hours, the frozen lung was cut into a thickness of 10–15 µl and put up on an APS-coated slide glass. For preparing a DIG-labeled probe, the ECF-L DNA fragment of 0.6 kb was amplified by PCR using the ECF-L full-length gene fragment obtained in EXAMPLE 1 as a template and using synthetic primers (PR3: SEQ ID NO:8, PR6: SEQ ID NO:11). Using Takara EX Taq (manufactured by Takara Shuzo Co., Ltd.), after incubation 94° C. for 1 minute, the reaction was carried out by repeating 30 cycles in Thermal Cycler Gene Amp PCR System 9700 (manufactured by Perkin-Elmer, Inc.), in which one cycle is set to include 94° C. for 10 seconds, 60° C. for 30 seconds and then 72° C. for90 seconds, and finally by reacting at 72° C. for 10 minutes. The amplified DNA fragment was inserted into PCRII-TOPO vector (manufactured by Invitrogen, Inc.), and extended from both sides of the vector by SF6 RNA polymerase and T7 RNA polymerase using DIG Labeling Kit (manufactured by Boehringer Mannheim) in accordance with the manual attached to prepare DIG-labeled antisense and sense probe. In situ hybridization was conducted using ISHR Starter Kit (manufactured by Nippon Gene Co., Ltd.) in accordance with the manual attached thereto. As a result, it was found that the ECF-L gene was highly expressed in the model mice with increased airway hyperresponsiveness. In the normal mice, no expression of the ECF-L gene was observed in any part of the lung (FIG. 6).

Example 5
Cloning of a Gene Encoding Human-derived ECF-L-like Protein

Using the mouse ECF-L full length gene shown in EXAMPLE 1 as a probe, Northern blotting analysis was performed on human RNA master blot (manufactured by Clontech Laboratories, Inc.). Hybridization was carried out at 68° C. for 2 hours in Express Hyb Hybridization Solution, and rinsing was finally made with 0.1×SSC in 0.1% SDS solution at 50° C. For detection, BAS-2000 (manufactured by Fuji Photo Film Co., Ltd.) was used. As a result, a marked signal was detected in the stomach. It was thus decided to acquire human counterpart of the ECF-L gene from human stomach cDNA library.

Figure 7:
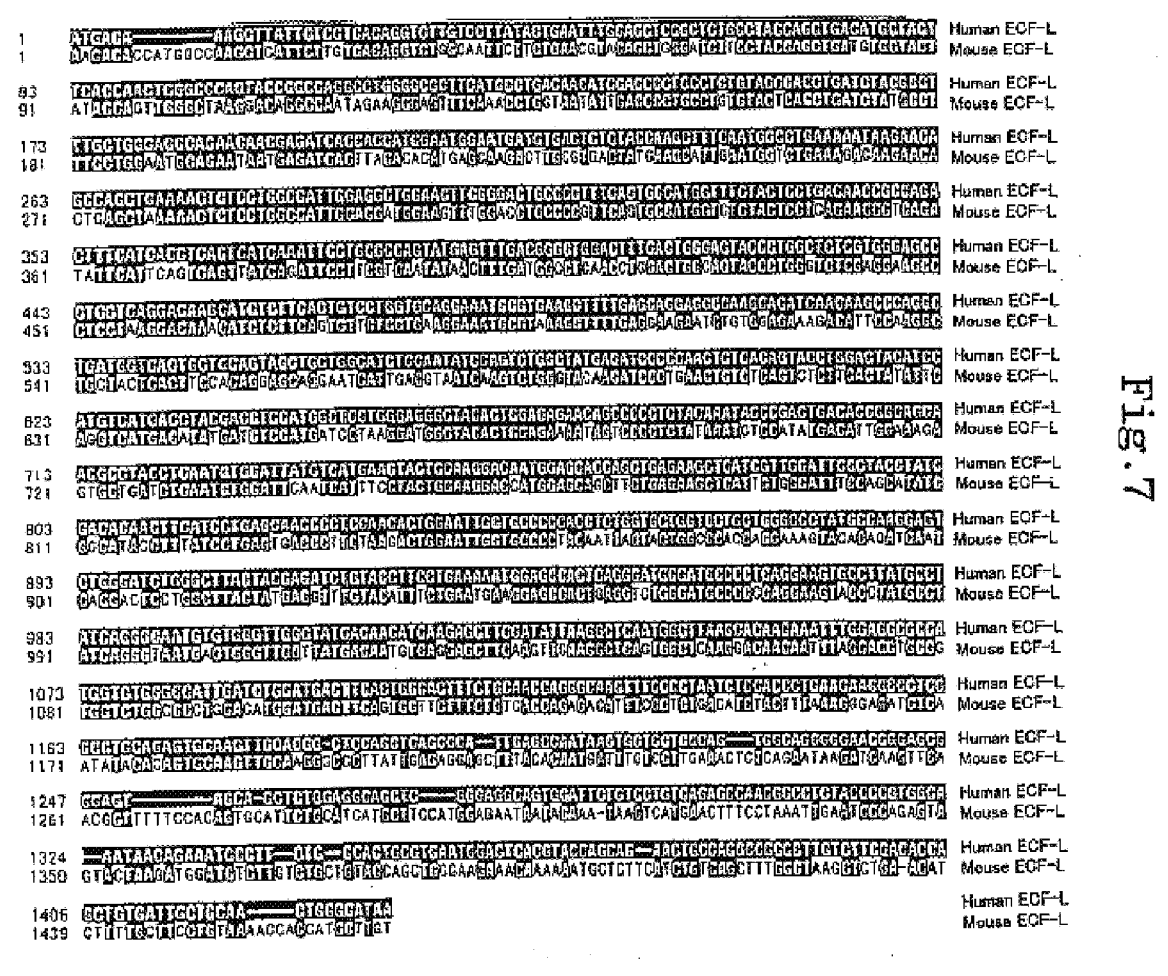
Figure 8:
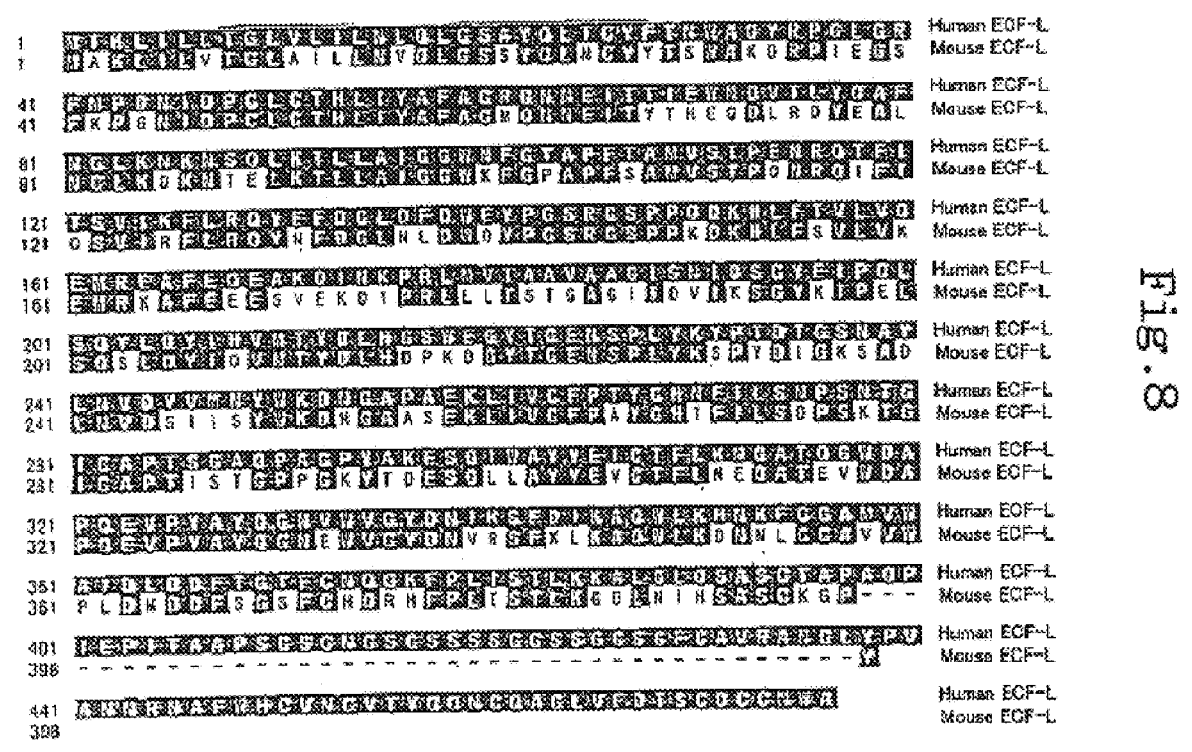
Figure 9:
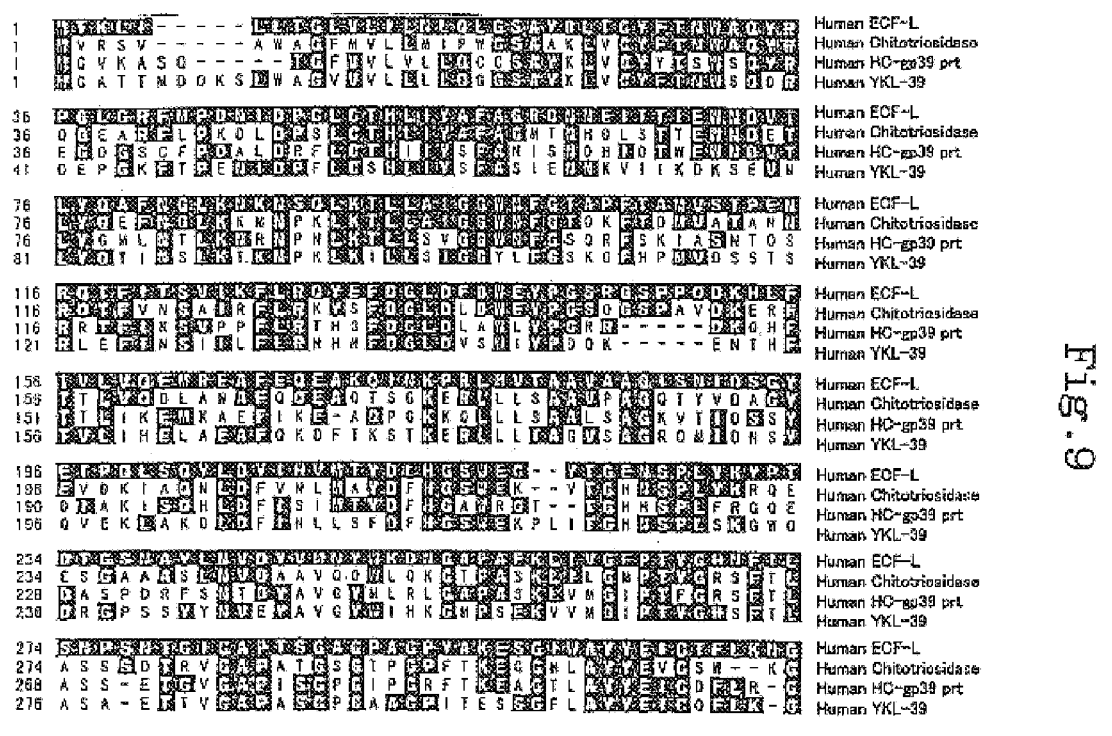
Figure 10:
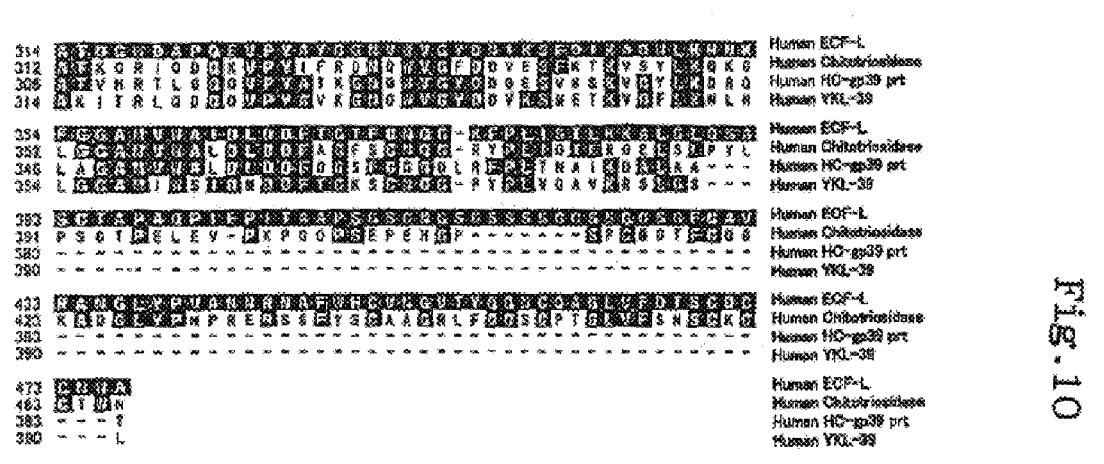

After human stomach 5'-stretch plus cDNA library (using λgt11 phage DNA as a vector, manufactured by Clontech Laboratories, Inc.) was infected to *E. coli* Y1090r⁻, about 200,000 plaques each was seeded in 7 soft agar plates and cultured overnight at 37° C. to form plaques. After the plaques were transferred to a nylon membrane filter (Hybond-N, made by Amersham Pharmacia Biotech, Inc.), the plaques were treated sequentially with a denaturation solution (0.5N NaOH, 1.5M NaCl), a neutralizing solution (0.5M Tris Cl pH 8.0, 1.5M NaCl) and 2×SSC. After air drying, UV rays were irradiated to fix phage DNA on the nylon membrane filter. Plaque hybridization was carried out at 68° C. for at least 3 hours in Express Hyb Hybridization Solution containing a labeled probe. After the filter was rinsed finally with 0.1×SSC in 0.1% SDS solution at 50° C., autoradiogram was taken to survey plaques hybridizable to the probe. Lambda DNA was prepared from 7 phage clones hECF-L-1, 2, 3, 10, 13, a and b, which were purified to single clones by repeating this procedure, using QIAGEN LAMBDA MINIKIT (manufactured by Qiagen) in accordance with the manual attached. Subsequently, a reaction was carried out using BigDye Terminator Cycle Sequencing Ready Reaction Kit (manufactured by Perkin-Elmer, Inc.), and the base sequence of the cDNA fragment inserted was determined using DNA Sequencer 377 (manufactured by Perkin-Elmer, Inc.). The results revealed that the 7 clones acquired contained the same DNA fragment and clone hECF-L-2 containing the longest DNA fragment had a 1678 bases (SEQ ID NO:16). The cDNA fragment encoded a human-derived new ECF-L-like protein consisting of 476 amino acids (SEQ ID NO:5). The protein had 70% homology in its base level and 68% homology in its amino acid level, to mouse ECF-L (FIGS. 7 and 8). Further homology search by blast N using the Geneble database revealed that the cDNA was a novel gene belonging to a chitinase (FIGS. 9 and 10). This protein has a sequence reserved at the catalytic center of chitinase, and showed 57% homology in the DNA level and 51% homology in the amino acid level, to human chitotrioxidase [J. Biol. Chem., 270, 26252 (1995)], which is reported to be the only one chitinase in human.

Example 6

Construction of Vector to Express a Gene Encoding Human-derived New ECF-L-like Protein in Animal Cells After Agtll phage DNA, in which the gene encoding human-derived ECF-L-like protein shown in EXAMPLE 5 had been inserted, was digested with EcoRI, the resulting DNA fragment of 1.7 kbp containing the gene encoding human-derived ECF-L-like protein was inserted into pcDNA 3.1 plasmid (manufactured by Invitrogen, Inc.) likewise digested with EcoRI to acquire plasmid pcDNA-hECFL bearing the gene encoding human-derived ECF-L-like protein downstream cytomegalovirus enhancer/promoter and having a neomycin resistant gene as a selection marker.

Example 7

Expression of the Gene Encoding Human-derived Novel ECF-L-like Protein in COS-7 Cells and Assay for Chitinase Activity COS-7 cells, 9×10⁵, were cultured for 24 hours in Dulbecco's Modified Eagle's medium (DMEM) supplemented with 10% fetal calf serum (FCS), and 7.5 μg of the expression plasmid (pcDNA-hECFL) shown in EXAMPLE 6 was transfected using lipofectamine (GIBCO BRL). Two days after the transfection, the medium was replaced with FCS-free DMEM and incubation was continued for 4 days to obtain the culture supernatant. The chitinase activity was assayed according to the report by Renkema, G. H. et al. [J. Biol. Chem., 20, 2198 (1995)]. That is, 100 μl of the culture supernatant described above was added to 100 μl of a reaction buffer (McIlvain buffer, pH 5.2), in which a fluorescent substrate (4-methylumbelliferyl β-D-N,N'-diacetylchitobioside (4MU-chitobioside), 4-methylumbellieryl β-D-N,N,N'-triacetylchitotrioside (4-MU-chitotrioside)) was dissolved in a final concentration of 0.027 mM, followed by incubation at 37° C. for 30 minutes. By adding 1 ml of a reaction termination buffer (0.3M glycine/NaOH buffer, pH10.6), the reaction was terminated, and chitinase activity was measured using a fluorescence measurement device (excited wavelength of 355 nm, measurement wavelength of 460 nm). For negative control, the culture supernatant from plasmid-non-transfected COS-7 cells was used and, 0.001 U of Serratia marcescens chitinase was used for positive control. As a result, the chitinase activity was detected in the culture supernatant from the expression plasmid (pcDNA-hECFL)-transfected COS-7 cells.

Example 8

Figure 11:
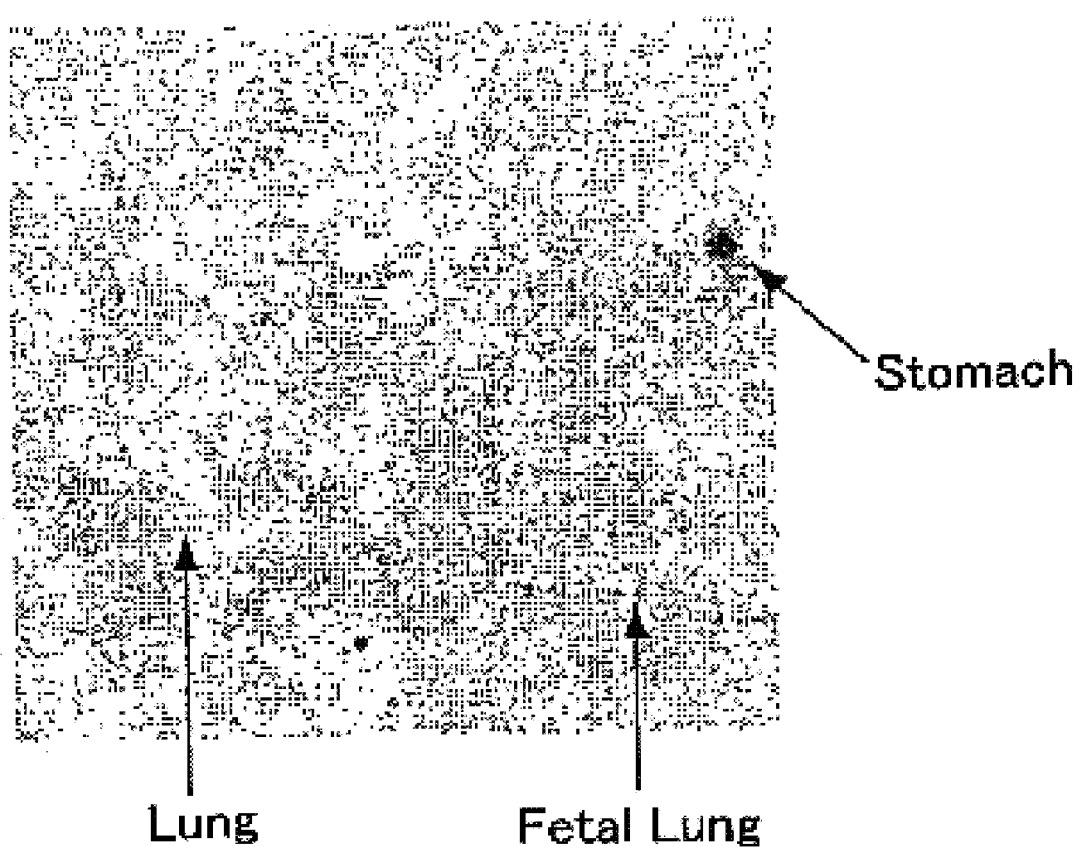
FIG. 11 shows tissue distribution of the gene (mRNA) encoding human-derived ECF-L like protein.

Analysis on Tissue Distribution of the Gene Encoding Human-derived Novel ECF-L-like Protein Using the DNA fragment (1.7 kbp) inserted with the gene encoding human-derived novel ECF-L-like protein shown in EXAMPLE 1 as a probe, Northern blotting analysis was performed on human RNA master blot (manufactured by clontech Laboratories, Inc.). Hybridization was carried out at 68° C. for 2 hours in Express Hyb Hybridization Solution containing a labeled probe, and rinsing was made finally with 0.1×SSC in 0.1% SDS solution at 50° C. For detection, BAS-2000 (manufactured by Fuji Photo Film Co., Ltd.) was used. As a result, a marked signal was detected in the stomach and the expression was observed also in the lung and embryonic lung (FIG. 11).

INDUSTRIAL APPLICABILITY

The protein of the present invention and the DNA encoding the same can be employed as therapeutic/prophylactic agents for diseases such as infectious diseases. The protein of the present invention is also useful as a reagent for screening a compound or its salts capable of promoting or inhibiting the activities of the protein of the present invention. Furthermore, a compound or its salts capable of inhibiting the activities of the protein of the present invention, or a neutralization antibody that inhibits the activities of the protein of the present invention can be used as therapeutic/prophylactic agents for diseases including bronchial asthma, chronic obstructive pulmonary disease, etc. Moreover, the antibodies against the protein of the present invention can recognize the protein of the present invention specifically and can be used for quantification of the protein of the present invention in a test sample fluid.

What is claimed is:

1. An isolated protein having the amino acid sequence represented by SEQ ID NO: 1, or a salt thereof.

2. An isolated signal peptide having the amino acid sequence represented by SEQ ID NO: 2, or a salt thereof.

3. An isolated polynucleotide comprising a DNA sequence encoding the protein according to claim 1 and having the base sequence represented by SEQ ID NO:3.

4. An isolated polynucleotide comprising a DNA sequence encoding the signal peptide according to claim 1 and having the base sequence represented by SEQ ID NO:4.

5. A recombinant vector comprising the DNA sequence according to claim 3.

6. A transformant transformed with the recombinant vector according to claim 5.

7. A method of manufacturing the protein according to claim 1 or a salt thereof, which comprises culturing a transformed host cell comprising an expressible DNA expression vector encoding for said protein, under conditions suitable for the expression of said protein for sufficient time to express said protein, and collecting the same.

8. A pharmaceutical comprising the protein according to claim 1 or a salt thereof, and a pharmaceutically acceptable carrier, diluent or excipient.

9. A pharmaceutical comprising the DNA according to claim 3, and a pharmaceutically acceptable carrier, excipient or diluent.

* * * * *

SEQUENCE LISTING

<160> NUMBER OF SEQ ID NOS: 18

<210> SEQ ID NO 1
<211> LENGTH: 455
<212> TYPE: PRT
<213> ORGANISM: Human

<400> SEQUENCE: 1

```
Tyr Gln Leu Thr Cys Tyr Phe Thr Asn Trp Ala Gln Tyr Arg Pro Gly
                 5                  10                  15

Leu Gly Arg Phe Met Pro Asp Asn Ile Asp Pro Cys Leu Cys Thr His
             20                  25                  30

Leu Ile Tyr Ala Phe Ala Gly Arg Gln Asn Asn Glu Ile Thr Thr Ile
         35                  40                  45

Glu Trp Asn Asp Val Thr Leu Tyr Gln Ala Phe Asn Gly Leu Lys Asn
 50                  55                  60

Lys Asn Ser Gln Leu Lys Thr Leu Leu Ala Ile Gly Gly Trp Asn Phe
 65                  70                  75                  80

Gly Thr Ala Pro Phe Thr Ala Met Val Ser Thr Pro Glu Asn Arg Gln
                 85                  90                  95

Thr Phe Ile Thr Ser Val Ile Lys Phe Leu Arg Gln Tyr Glu Phe Asp
            100                 105                 110

Gly Leu Asp Phe Asp Trp Glu Tyr Pro Gly Ser Arg Gly Ser Pro Pro
        115                 120                 125

Gln Asp Lys His Leu Phe Thr Val Leu Val Gln Glu Met Arg Glu Ala
130                 135                 140

Phe Glu Gln Glu Ala Lys Gln Ile Asn Lys Pro Arg Leu Met Val Thr
145                 150                 155                 160

Ala Ala Val Ala Ala Gly Ile Ser Asn Ile Gln Ser Gly Tyr Glu Ile
                165                 170                 175

Pro Gln Leu Ser Gln Tyr Leu Asp Tyr Ile His Val Met Thr Tyr Asp
            180                 185                 190

Leu His Gly Ser Trp Glu Gly Tyr Thr Gly Glu Asn Ser Pro Leu Tyr
        195                 200                 205

Lys Tyr Pro Thr Asp Thr Gly Ser Asn Ala Tyr Leu Asn Val Asp Tyr
    210                 215                 220

Val Met Asn Tyr Trp Lys Asp Asn Gly Ala Pro Ala Glu Lys Leu Ile
225                 230                 235                 240

Val Gly Phe Pro Thr Tyr Gly His Asn Phe Ile Leu Ser Asn Pro Ser
                245                 250                 255

Asn Thr Gly Ile Gly Ala Pro Thr Ser Gly Ala Gly Pro Ala Gly Pro
            260                 265                 270

Tyr Ala Lys Glu Ser Gly Ile Trp Ala Tyr Tyr Glu Ile Cys Thr Phe
        275                 280                 285

Leu Lys Asn Gly Ala Thr Gln Gly Trp Asp Ala Pro Gln Glu Val Pro
    290                 295                 300

Tyr Ala Tyr Gln Gly Asn Val Trp Val Gly Tyr Asp Asn Ile Lys Ser
305                 310                 315                 320

Phe Asp Ile Lys Ala Gln Trp Leu Lys His Asn Lys Phe Gly Gly Ala
                325                 330                 335

Met Val Trp Ala Ile Asp Leu Asp Asp Phe Thr Gly Thr Phe Cys Asn
            340                 345                 350

Gln Gly Lys Phe Pro Leu Ile Ser Thr Leu Lys Lys Ala Leu Gly Leu
```

```
                355             360             365
Gln Ser Ala Ser Cys Thr Ala Pro Ala Gln Pro Ile Glu Pro Ile Thr
        370                 375                 380

Ala Ala Pro Ser Gly Ser Gly Asn Gly Ser Gly Ser Ser Ser Ser Gly
385                 390                 395                 400

Gly Ser Ser Gly Gly Ser Gly Phe Cys Ala Val Arg Ala Asn Gly Leu
                405                 410                 415

Tyr Pro Val Ala Asn Asn Arg Asn Ala Phe Trp His Cys Val Asn Gly
                420                 425                 430

Val Thr Tyr Gln Gln Asn Cys Gln Ala Gly Leu Val Phe Asp Thr Ser
            435                 440                 445

Cys Asp Cys Cys Asn Trp Ala
        450                 455

<210> SEQ ID NO 2
<211> LENGTH: 21
<212> TYPE: PRT
<213> ORGANISM: Human

<400> SEQUENCE: 2

Met Thr Lys Leu Ile Leu Leu Thr Gly Leu Val Leu Ile Leu Asn Leu
                5                   10                  15

Gln Leu Gly Ser Ala
            20

<210> SEQ ID NO 3
<211> LENGTH: 1368
<212> TYPE: DNA
<213> ORGANISM: Human

<400> SEQUENCE: 3
taccagctga catgctactt caccaactgg gcccagtacc ggccaggcct ggggcgcttc      60
atgcctgaca acatcgaccc ctgcctctgt acccacctga tctacgcctt tgctgggagg     120
cagaacaacg agatcaccac catcgaatgg aatgatgtga ctctctacca agctttcaat     180
ggcctgaaaa ataagaacag ccagctgaaa actctcctgg ccattggagg ctggaacttc     240
gggactgccc ctttcactgc catggttttct actcctgaga accgccagac tttcatcacc     300
tcagtcatca aattcctgcg ccagtatgag tttgacgggc tggactttga ctgggagtac     360
cctggctctc gtgggagccc tcctcaggac aagcatctct tcactgtcct ggtgcaggaa     420
atgcgtgaag cttttgagca ggaggccaag cagatcaaca gcccaggct gatggtcact      480
gctgcagtag ctgctggcat ctccaatatc cagtctggct atgagatccc ccaactgtca     540
cagtacctgg actacatcca tgtcatgacc tacgacctcc atggctcctg ggagggctac     600
actggagaga cagccccct ctacaaatac ccgactgaca ccggcagcaa cgcctacctc      660
aatgtggatt atgtcatgaa ctactggaag acaatggag caccagctga aagctcatc      720
gttggattcc ctacctatgg acacaacttc atcctgagca ccctccaa cactggaatt       780
ggtgccccca cctctggtgc tggtcctgct gggccctatg ccaaggagtc tgggatctgg     840
gcttactacg agatctgtac cttcctgaaa atggagcca ctcagggatg ggatgcccct      900
caggaagtgc cttatgccta tcagggcaat gtgtgggttg ctatgacaa catcaagagc      960
ttcgatatta aggctcaatg gcttaagcac aacaaatttg gaggcgccat ggtctgggcc    1020
attgatctgg atgacttcac tggcacttttc tgcaaccagg gcaagtttcc cctaatctcc    1080
accctgaaga aggccctcgg cctgcagagt gcaagttgca cggctccagc tcagcccatt    1140
```

-continued

```
gagccaataa ctgctgctcc cagtggcagc gggaacggga gcgggagtag cagctctgga    1200
ggcagctcgg gaggcagtgg attctgtgct gtcagagcca acggcctcta ccccgtggca    1260
aataacagaa atgccttctg cactgcgtg aatggagtca cgtaccagca gaactgccag     1320
gccgggcttg tcttcgacac cagctgtgat tgctgcaact gggcataa                 1368
```

<210> SEQ ID NO 4
<211> LENGTH: 63
<212> TYPE: DNA
<213> ORGANISM: Human

<400> SEQUENCE: 4

```
atgacaaagc ttattctcct cacaggtctt gtccttatac tgaatttgca gctcggctct    60
gcc                                                                   63
```

<210> SEQ ID NO 5
<211> LENGTH: 476
<212> TYPE: PRT
<213> ORGANISM: Human

<400> SEQUENCE: 5

```
Met Thr Lys Leu Ile Leu Leu Thr Gly Leu Val Leu Ile Leu Asn Leu
              5                   10                  15

Gln Leu Gly Ser Ala Tyr Gln Leu Thr Cys Tyr Phe Thr Asn Trp Ala
         20                  25                  30

Gln Tyr Arg Pro Gly Leu Gly Arg Phe Met Pro Asp Asn Ile Asp Pro
     35                  40                  45

Cys Leu Cys Thr His Leu Ile Tyr Ala Phe Ala Gly Arg Gln Asn Asn
 50                  55                  60

Glu Ile Thr Thr Ile Glu Trp Asn Asp Val Thr Leu Tyr Gln Ala Phe
 65                  70                  75                  80

Asn Gly Leu Lys Asn Lys Asn Ser Gln Leu Lys Thr Leu Leu Ala Ile
                 85                  90                  95

Gly Gly Trp Asn Phe Gly Thr Ala Pro Phe Thr Ala Met Val Ser Thr
            100                 105                 110

Pro Glu Asn Arg Gln Thr Phe Ile Thr Ser Val Ile Lys Phe Leu Arg
        115                 120                 125

Gln Tyr Glu Phe Asp Gly Leu Asp Phe Asp Trp Glu Tyr Pro Gly Ser
    130                 135                 140

Arg Gly Ser Pro Pro Gln Asp Lys His Leu Phe Thr Val Leu Val Gln
145                 150                 155                 160

Glu Met Arg Glu Ala Phe Glu Gln Glu Ala Lys Gln Ile Asn Lys Pro
                165                 170                 175

Arg Leu Met Val Thr Ala Ala Val Ala Ala Gly Ile Ser Asn Ile Gln
            180                 185                 190

Ser Gly Tyr Glu Ile Pro Gln Leu Ser Gln Tyr Leu Asp Tyr Ile His
        195                 200                 205

Val Met Thr Tyr Asp Leu His Gly Ser Trp Glu Gly Tyr Thr Gly Glu
    210                 215                 220

Asn Ser Pro Leu Tyr Lys Tyr Pro Thr Asp Thr Gly Ser Asn Ala Tyr
225                 230                 235                 240

Leu Asn Val Asp Tyr Val Met Asn Tyr Trp Lys Asp Asn Gly Ala Pro
                245                 250                 255

Ala Glu Lys Leu Ile Val Gly Phe Pro Thr Tyr Gly His Asn Phe Ile
            260                 265                 270
```

```
Leu Ser Asn Pro Ser Asn Thr Gly Ile Gly Ala Pro Thr Ser Gly Ala
            275                 280                 285

Gly Pro Ala Gly Pro Tyr Ala Lys Glu Ser Gly Ile Trp Ala Tyr Tyr
        290                 295                 300

Glu Ile Cys Thr Phe Leu Lys Asn Gly Ala Thr Gln Gly Trp Asp Ala
305                 310                 315                 320

Pro Gln Glu Val Pro Tyr Ala Tyr Gln Gly Asn Val Trp Val Gly Tyr
                325                 330                 335

Asp Asn Ile Lys Ser Phe Asp Ile Lys Ala Gln Trp Leu Lys His Asn
            340                 345                 350

Lys Phe Gly Gly Ala Met Val Trp Ala Ile Asp Leu Asp Asp Phe Thr
        355                 360                 365

Gly Thr Phe Cys Asn Gln Gly Lys Phe Pro Leu Ile Ser Thr Leu Lys
        370                 375                 380

Lys Ala Leu Gly Leu Gln Ser Ala Ser Cys Thr Ala Pro Ala Gln Pro
385                 390                 395                 400

Ile Glu Pro Ile Thr Ala Ala Pro Ser Gly Ser Gly Asn Gly Ser Gly
                405                 410                 415

Ser Ser Ser Ser Gly Gly Ser Ser Gly Gly Ser Gly Phe Cys Ala Val
                420                 425                 430

Arg Ala Asn Gly Leu Tyr Pro Val Ala Asn Asn Arg Asn Ala Phe Trp
            435                 440                 445

His Cys Val Asn Gly Val Thr Tyr Gln Gln Asn Cys Gln Ala Gly Leu
        450                 455                 460

Val Phe Asp Thr Ser Cys Asp Cys Cys Asn Trp Ala
465                 470                 475

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
aagacaccat ggccaagctc                                                 20

<210> SEQ ID NO 7
<211> LENGTH: 24
<212> TYPE: DNA
<213> ORGANISM: Artificial Sequence
<220> FEATURE:
<223> OTHER INFORMATION: Primer

<400> SEQUENCE: 7
acaagcatgg tggttttaca ggaa                                            24

<210> SEQ ID NO 8
<211> LENGTH: 18
<212> TYPE: DNA
<213> ORGANISM: Artificial Sequence
<220> FEATURE:
<223> OTHER INFORMATION: Primer

<400> SEQUENCE: 8
tggtgaagga aatgcgta                                                   18

<210> SEQ ID NO 9
<211> LENGTH: 19
```

```
<212> TYPE: DNA
<213> ORGANISM: Artificial Sequence
<220> FEATURE:
<223> OTHER INFORMATION: Primer

<400> SEQUENCE: 9
ttacgcattt ccttcacca                                                  19

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
atttaggagg tgccgtggt                                                  19

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gaccacggca cctcctaaat                                                 20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
tactcctcag aaccgtcaga                                                 20

<210> SEQ ID NO 13
<211> LENGTH: 20
<212> TYPE: DNA
<213> ORGANISM: Artificial Sequence
<220> FEATURE:
<223> OTHER INFORMATION: Primer

<400> SEQUENCE: 13
ctccagtgta gccatcctta                                                 20

<210> SEQ ID NO 14
<211> LENGTH: 1469
<212> TYPE: DNA
<213> ORGANISM: Mouse

<400> SEQUENCE: 14
aagacaccat ggccaagctc attcttgtca caggtctggc aattcttctg aacgtacagc      60
tgggatcttc ctaccagctg atgtgctact ataccagttg ggctaaggac aggccaatag     120
aagggagttt caaacctggt aatattgacc cctgcctgtg tactcacctg atctatgcct     180
ttgctggaat gcagaataat gagatcactt acacacatga gcaagacttg cgtgactatg     240
aagcattgaa tggtctgaaa gacaagaaca ctgagctaaa aactctcctg gccattggag     300
gatggaagtt tggacctgcc ccgttcagtg ccatggtctc tactcctcag aaccgtcaga     360
tattcattca gtcagttatc agattccttc gtcaatataa ctttgatggc ctcaacctgg     420
```

```
actggcagta ccctgggtct cgaggaagcc ctcctaagga caaacatctc ttcagtgttc      480
tggtgaagga aatgcgtaaa gcttttgagg aagaatctgt ggagaaagac attccaaggc      540
tgctactcac ttccacagga gcaggaatca ttgacgtaat caagtctggg tacaagatcc      600
ctgaactgtc tcagtctctt gactatattc aggtcatgac atatgatctc catgatccta      660
aggatggcta cactgagaa atagtcccc tctataaatc tccatatgac attggaaaga       720
gtgctgatct caatgtggat tcaatcattt cctactggaa ggaccatgga gcagcttctg      780
agaagctcat tgtgggattt ccagcatatg gcataccttt atcctgagt gacccttcta       840 agactggaat tggtgcccct acaattagta ctggcccacc aggaaagtac acagatgaat      900
caggactcct ggcttactat gaggtttgta catttctgaa tgaaggagcc actgaggtct      960
gggatgcccc ccaggaagta ccctatgcct atcagggtaa tgagtgggtt ggttatgaca     1020
atgtcaggag cttcaagttg aaggctcagt ggcttaagga caacaattta ggaggtgccg     1080
tggtctggcc cctggacatg gatgacttca gtggttcttt ctgtcaccag agacatttcc     1140
ctctgacatc tactttaaag ggagatctca atatacacag tgcaagttgc aagggccctt     1200
attgagagga gctttacaca atgatttgtc cttgaaactc tcagaataag atcaagttca     1260 acggttttc cacagtgcat tctgcatcat gcttccatgg agaataatag aaataagtca      1320
tgaactttcc taaattgaat cccagagtag tactaagatg gatgtcttgt ctgctgtacc     1380
agctgggaag aaacaaaaaa tgctcttcat ctgtcagctt tggctaagct ctgaacatct     1440
tttgcttcct gtaaaaccac catgcttgt                                       1469

<210> SEQ ID NO 15
<211> LENGTH: 369
<212> TYPE: DNA
<213> ORGANISM: Artificial Sequence
<220> FEATURE:
<223> OTHER INFORMATION: Primer

<400> SEQUENCE: 15
accctatgcc tatcagggta atgagtgggt tggttatgac aatgtcagga gcttcaagtt       60
gaaggctcag tggcttaagg acaacaattt aggaggtgcc gtggtctggc cctggacat      120 ggatgacttc agtggttctt tctgtcacca gagacatttc cctctgacat ctactttaaa     180
gggagatctc aatatacaca gtgcaagttg caagggctct tattgagagg agctttacac     240
aatgatttgt cctgaaactc tcagaataag atcaagttca acggttttc cacaggcatt     300 ctgcatcatg cttccatgga gaataataga ataagtcat gaacttttcct aaatgaatcc     360 cagagtagt                                                            369

<210> SEQ ID NO 16
<211> LENGTH: 1678
<212> TYPE: DNA
<213> ORGANISM: Human

<400> SEQUENCE: 16
gaattccggg caaaaaggtc atccaaggag gaagccgaga tggcctacaa agacttcctg       60
ctccagtcca gcaccgtggc cgccgaggcc caggacggcc cccaggaagc ctagacggtg      120
tcgccgcctg ctccctgcac ccatgacaaa gcttattctc ctcacaggtc ttgtccttat      180
actgaatttg cagctcggct ctgcctacca gctgacatgc tacttcacca actgggccca      240
gtaccggcca ggcctgggc gcttcatgcc tgacaacatc gacccctgcc tctgtaccca      300
cctgatctac gcctttgctg ggaggcagaa caacgagatc accaccatcg aatggaatga     360
```

-continued

```
tgtgactctc taccaagctt tcaatggcct gaaaaataag aacagccagc tgaaaactct    420
cctggccatt ggaggctgga acttcgggac tgccccttc actgccatgg tttctactcc    480
tgagaaccgc cagactttca tcacctcagt catcaaattc ctgcgccagt atgagtttga   540
cgggctggac tttgactggg agtaccctgg ctctcgtggg agccctcctc aggacaagca   600
tctcttcact gtcctggtgc aggaaatgcg tgaagctttt gagcaggagg ccaagcagat   660
caacaagccc aggctgatgg tcactgctgc agtagctgct ggcatctcca atatccagtc   720
tggctatgag atccccaac tgtcacagta cctggactac atccatgtca tgacctacga   780
cctccatggc tcctgggagg gctacactgg agagaacagc ccctctaca aatacccgac    840
tgacaccggc agcaacgcct acctcaatgt ggattatgtc atgaactact ggaaggacaa   900
tggagcacca gctgagaagc tcatcgttgg attccctacc tatggacaca acttcatcct   960
gagcaacccc tccaacactg gaattggtgc ccccacctct ggtgctggtc ctgctgggcc  1020
ctatgccaag gagtctggga tctgggctta ctacgagatc tgtaccttcc tgaaaaatgg  1080
agccactcag ggatgggatg cccctcagga agtgccttat gcctatcagg caatgtgtg   1140
ggttggctat gacaacatca agagcttcga tattaaggct caatggctta agcacaacaa  1200
atttggaggc gccatggtct gggccattga tctggatgac ttcactgcca ctttctgcaa  1260
ccagggcaag tttcccctaa tctccaccct gaagaaggcc ctcggcctgc agagtgcaag  1320
ttgcacggct ccagctcagc ccattgagcc aataactgct gctcccagtg gcagcgggaa  1380
cgggagcggg agtagcagct ctggaggcag ctcgggaggc agtggattct gtgctgtcag  1440
agccaacggc ctctaccccg tgcaaataa cagaaatgcc ttctggcact gcgtgaatgg  1500
agtcacgtac cagcagaact gccaggccgg gcttgtcttc gacaccagct gtgattgctg  1560
caactgggca taaacctgac ctggtctata ttccctagag ttccagtctc ttttgcttag  1620
gacatgttgc ccctacctaa agtcctgcaa taaaatcagc agtcaaaacc cggaattc    1678
```

<210> SEQ ID NO 17
<211> LENGTH: 398
<212> TYPE: PRT
<213> ORGANISM: Mouse

<400> SEQUENCE: 17

```
Met Ala Lys Leu Ile Leu Val Thr Gly Leu Ala Ile Leu Leu Asn Val
  1               5                  10                  15

Gln Leu Gly Ser Ser Tyr Gln Leu Met Cys Tyr Tyr Thr Ser Trp Ala
             20                  25                  30

Lys Asp Arg Pro Ile Glu Gly Ser Phe Lys Pro Gly Asn Ile Asp Pro
         35                  40                  45

Cys Leu Cys Thr His Leu Ile Tyr Ala Phe Ala Gly Met Gln Asn Asn
     50                  55                  60

Glu Ile Thr Tyr Thr His Glu Gln Asp Leu Arg Asp Tyr Glu Ala Leu
 65                  70                  75                  80

Asn Gly Leu Lys Asp Lys Asn Thr Glu Leu Lys Thr Leu Leu Ala Ile
                 85                  90                  95

Gly Gly Trp Lys Phe Gly Pro Ala Pro Phe Ser Ala Met Val Ser Thr
            100                 105                 110

Pro Gln Asn Arg Gln Ile Phe Ile Gln Ser Val Ile Arg Phe Leu Arg
        115                 120                 125

Gln Tyr Asn Phe Asp Gly Leu Asn Leu Asp Trp Gln Tyr Pro Gly Ser
    130                 135                 140
```

-continued

```
Arg Gly Ser Pro Pro Lys Asp Lys His Leu Phe Ser Val Leu Val Lys
145                 150                 155                 160

Glu Met Arg Lys Ala Phe Glu Glu Ser Val Glu Lys Asp Ile Pro
            165                 170                 175

Arg Leu Leu Thr Ser Thr Gly Ala Gly Ile Ile Asp Val Ile Lys
            180                 185                 190

Ser Gly Tyr Lys Ile Pro Glu Leu Ser Gln Ser Leu Asp Tyr Ile Gln
            195                 200                 205

Val Met Thr Tyr Asp Leu His Asp Pro Lys Asp Gly Tyr Thr Gly Glu
210                 215                 220

Asn Ser Pro Leu Tyr Lys Ser Pro Tyr Asp Ile Gly Lys Ser Ala Asp
225                 230                 235                 240

Leu Asn Val Asp Ser Ile Ile Ser Tyr Trp Lys Asp His Gly Ala Ala
                245                 250                 255

Ser Glu Lys Leu Ile Val Gly Phe Pro Ala Tyr Gly His Thr Phe Ile
            260                 265                 270

Leu Ser Asp Pro Ser Lys Thr Gly Ile Gly Ala Pro Thr Ile Ser Thr
275                 280                 285

Gly Pro Pro Gly Lys Tyr Thr Asp Glu Ser Gly Leu Leu Ala Tyr Tyr
290                 295                 300

Glu Val Cys Thr Phe Leu Asn Glu Gly Ala Thr Glu Val Trp Asp Ala
305                 310                 315                 320

Pro Gln Glu Val Pro Tyr Ala Tyr Gln Gly Asn Glu Trp Val Gly Tyr
            325                 330                 335

Asp Asn Val Arg Ser Phe Lys Leu Lys Ala Gln Trp Leu Lys Asp Asn
            340                 345                 350

Asn Leu Gly Gly Ala Val Val Trp Pro Leu Asp Met Asp Asp Phe Ser
            355                 360                 365

Gly Ser Phe Cys His Gln Arg His Phe Pro Leu Thr Ser Thr Leu Lys
370                 375                 380

Gly Asp Leu Asn Ile His Ser Ala Ser Cys Lys Gly Pro Tyr
385                 390                 395

<210> SEQ ID NO 18
<211> LENGTH: 377
<212> TYPE: PRT
<213> ORGANISM: Mouse

<400> SEQUENCE: 18

Tyr Gln Leu Met Cys Tyr Tyr Thr Ser Trp Ala Lys Asp Arg Pro Ile
                5                   10                  15

Glu Gly Ser Phe Lys Pro Gly Asn Ile Asp Pro Cys Leu Cys Thr His
            20                  25                  30

Leu Ile Tyr Ala Phe Ala Gly Met Gln Asn Asn Glu Ile Thr Tyr Thr
        35                  40                  45

His Glu Gln Asp Leu Arg Asp Tyr Glu Ala Leu Asn Gly Leu Lys Asp
    50                  55                  60

Lys Asn Thr Glu Leu Lys Thr Leu Leu Ala Ile Gly Gly Trp Lys Phe
65                  70                  75                  80

Gly Pro Ala Pro Phe Ser Ala Met Val Ser Thr Pro Gln Asn Arg Gln
                85                  90                  95

Ile Phe Ile Gln Ser Val Ile Arg Phe Leu Arg Gln Tyr Asn Phe Asp
            100                 105                 110

Gly Leu Asn Leu Asp Trp Gln Tyr Pro Gly Ser Arg Gly Ser Pro Pro
```

-continued

```
                115                 120                 125
Lys Asp Lys His Leu Phe Ser Val Leu Val Lys Glu Met Arg Lys Ala
    130                 135                 140

Phe Glu Glu Glu Ser Val Glu Lys Asp Ile Pro Arg Leu Leu Leu Thr
145                 150                 155                 160

Ser Thr Gly Ala Gly Ile Ile Asp Val Ile Lys Ser Gly Tyr Lys Ile
                165                 170                 175

Pro Glu Leu Ser Gln Ser Leu Asp Tyr Ile Gln Val Met Thr Tyr Asp
                180                 185                 190

Leu His Asp Pro Lys Asp Gly Tyr Thr Gly Glu Asn Ser Pro Leu Tyr
        195                 200                 205

Lys Ser Pro Tyr Asp Ile Gly Lys Ser Ala Asp Leu Asn Val Asp Ser
    210                 215                 220

Ile Ile Ser Tyr Trp Lys Asp His Gly Ala Ala Ser Glu Lys Leu Ile
225                 230                 235                 240

Val Gly Phe Pro Ala Tyr Gly His Thr Phe Ile Leu Ser Asp Pro Ser
                245                 250                 255

Lys Thr Gly Ile Gly Ala Pro Thr Ile Ser Thr Gly Pro Pro Gly Lys
                260                 265                 270

Tyr Thr Asp Glu Ser Gly Leu Leu Ala Tyr Tyr Glu Val Cys Thr Phe
        275                 280                 285

Leu Asn Glu Gly Ala Thr Glu Val Trp Asp Ala Pro Gln Glu Val Pro
    290                 295                 300

Tyr Ala Tyr Gln Gly Asn Glu Trp Val Gly Tyr Asp Asn Val Arg Ser
305                 310                 315                 320

Phe Lys Leu Lys Ala Gln Trp Leu Lys Asp Asn Asn Leu Gly Gly Ala
                325                 330                 335

Val Val Trp Pro Leu Asp Met Asp Asp Phe Ser Gly Ser Phe Cys His
                340                 345                 350

Gln Arg His Phe Pro Leu Thr Ser Thr Leu Lys Gly Asp Leu Asn Ile
        355                 360                 365

His Ser Ala Ser Cys Lys Gly Pro Tyr
370                 375
```